US007884192B2

(12) United States Patent
Bron et al.

(10) Patent No.: US 7,884,192 B2
(45) Date of Patent: *Feb. 8, 2011

(54) TWIN-ARGININE TRANSLOCATION IN BACILLUS

(75) Inventors: Sierd Bron, Haren (NL); Jan D. H. Jongbloed, Groningen (NL); Joerg Muller, Jena (DE); Jan M. Van Dijl, Harkstede (NL)

(73) Assignee: Danisco US Inc., Palo Alto, CA (US)

( * ) Notice: Subject to any disclaimer, the term of this patent is extended or adjusted under 35 U.S.C. 154(b) by 169 days.

This patent is subject to a terminal disclaimer.

(21) Appl. No.: 11/809,669

(22) Filed: Jun. 1, 2007

(65) Prior Publication Data

US 2008/0166757 A1 Jul. 10, 2008

Related U.S. Application Data

(62) Division of application No. 09/954,737, filed on Sep. 17, 2001, now Pat. No. 7,316,924.

(60) Provisional application No. 60/233,610, filed on Sep. 18, 2000.

(51) Int. Cl.
*C07K 14/32* (2006.01)
*C12N 9/00* (2006.01)
*A61K 39/00* (2006.01)

(52) U.S. Cl. ............... 530/350; 435/183; 424/192.1

(58) Field of Classification Search ............... None
See application file for complete search history.

(56) References Cited

U.S. PATENT DOCUMENTS

| 3,817,837 | A | 6/1974 | Rubenstein et al. ...... 195/103.5 |
| 3,850,752 | A | 11/1974 | Schuurs et al. ........... 195/103.5 |
| 3,939,350 | A | 2/1976 | Kronick et al. ............ 250/365 |
| 3,996,345 | A | 12/1976 | Ullman et al. ................ 424/12 |
| 4,275,149 | A | 6/1981 | Litman et al. .................. 435/7 |
| 4,277,437 | A | 7/1981 | Maggio ....................... 422/61 |
| 4,366,241 | A | 12/1982 | Tom et al. ...................... 435/7 |
| 4,816,567 | A | 3/1989 | Cabilly et al. ............... 530/387 |
| 5,641,671 | A * | 6/1997 | Bos et al. .................... 435/198 |
| 5,804,409 | A | 9/1998 | Bos et al. |
| 7,214,773 | B2 | 5/2007 | Kolkman |

FOREIGN PATENT DOCUMENTS

| EP | 0 444 759 A1 | 9/1991 |
| WO | WO 99/51753 | 10/1999 |
| WO | WO 02/055717 A2 | 7/2002 |

OTHER PUBLICATIONS

*Altschul el al., "Gapped BLAST and PSI-BLAST: a new generation of protein database programs," Nucl. Acids Res., vol. 25, pp. 3389-3402, 1997.

*Antelmann el al., "Expression of a Stress- and Starvation-induced dps/pexB—Homologous Gene Is Controlled by the Alternative Sigma Factor $\sigma^B$ in *Bacillus bacillus*," J. of Bacteriology, vol. 179, pp. 7251-7256, 1997.
*Antelmann el al., "Phosphate Starvation-Inducible Proteins of *Bacillus bacillus*: Proteomics and Transcriptional Analysis," J. of Bacteriology, vol. 182, pp. 4478-4490, 2000.
*Bakhiet et al., "Studies on Transfection and Transformation of Protoplasts of *Bacillus larvae, Bacillus subtilis*, and *Bacillus popilliae*," Applied and Environmental Microbiology, vol. 49, No. 3, pp. 577-581, Mar. 1985.
*Benton et al., "Steering λgt Recombinant Clones by Hybridization to Single Plaques in situ," Science, vol. 196, No. 4286, pp. 180-182, Apr. 8, 1977.
*Berger and Kimmel, Guide to Molecular Cloning Techniques, Methods in Enzymology, vol. 152, Academic Press, San Diego, CA (1987).
*Berks B., "A common export pathway for proteins binding complex redox cofactors," Mol Microbiol. vol. 22, pp. 393-404, 1996.
*Berks et al., "The Tat protein export pathway," Mol Microbiol. vol. 35, pp. 260-274, 2000.
*Bernhardt et al., "Specific and general stress proteins in *Bacillus subtilis*—a two-dimensional protein electrophoresis study," Microbiol. vol. 143, pp. 999-1017, 1997.
*Database EMBL, Blattner F.R. et al., << Hypothetical 11.3 KD Protein in UDP-RFAH Intergenic Region (TATA Protein), Database accession No. 065938, XP002133194.
*Blum et al., "Improved silver staining of plant proteins, RNA and DNA in polyacrylamide gels," Electrophoresis, vol. 8, pp. 93-99, 1987.
*Bogsch et al., "Pathway specificity for a ΔpH-dependent precursor thylakoid lumen protein is governed by a 'Sec-avoidance' motif in the transfer peptide and a 'Sec-incompatible' mature protein," EMBO, vol. 16, pp. 3851-3859, 1997.
*Bogsch et al., "An Essential Component of a Novel Bacterial Protein Export System with Homologues in Plastids and Mitochondria," J. Biol. Chem., vol. 273, pp. 18003-18006, 1998.
*Bolhuis et al., "Evaluation of Bottlenecks in the Late Stages of Protein Secretion in *Bacillus subtilis*," App. Environ. Microbiol. vol. 65, pp. 2934-2941, 1999.
*Bolhuis et al., "Different Mechanisms for Thermal Inactivation of *Bacillus subtilis* Signal Mutants," J. Biolog. Chem., vol. 274, pp. 15865-15868, 1999.
*Bolhuis et al., "*Bacillus subtilis*, can modulate its capacity and specificity for protein secretion through temporally controlled expression of the *sipS* gene for signal peptidase I" Mol. Microbiol. vol. 22, pp. 605-618, 1996.

(Continued)

*Primary Examiner*—Michael Burkhart
(74) *Attorney, Agent, or Firm*—Margaret A. Powers; Danisco US Inc.; Morrison & Foerster LLP

(57) ABSTRACT

Described herein are methods to enhance protein secretion in a host cell. In preferred embodiment, the host cell is a gram-positive microorganism such as a *Bacillus*. In another preferred embodiment, the host cell is a gram-negative microorganism. Preferably the gram-negative microorganism is an *Escherichia coli* or a member of the genus *Pantoea*. Protein secretion may be enhanced by the overexpression of protein components of the Tat pathway. Alternatively, secretion of foreign proteins can be selectively enhanced by forming a chimeric polypeptide comprising a tat signal sequence and the protein of interest. In a preferred embodiment, the tat signal sequence is selected from phoD or LipA.

16 Claims, 11 Drawing Sheets

OTHER PUBLICATIONS

*Brink et al., "Targeting of thylakoid proteins by the ΔpH-driven twin-arginine translocation pathway requires a specific signal in the hydrophobic domain in conjunction with the twin-arginine motif," FEBS Letters, vol. 434, pp. 425-430, 1998.

*Bron et al., "Construction and Characterization of a Transformable Eightfold Auxotrophic Strain and two Ultraviolet-Sensitive Derivatives," Mutation Research, vol. 15, pp. 1-10, 1972.

*Chaddock et al., "A new type of signal peptide: central role of a twin-arginine motif in transfer signals for the ΔpH-dependent thylakoid protein translocase," EMBO, vol. 14, pp. 2715-2722, 1995.

*Chanal et al., "MicroCorrespondence," Molec. Microbiol. vol. 30, pp. 673-678, 1998.

*Chang et al., "High Frequency Transformation of Bacillus subtilis Protoplasts by Plasmid DNA," Molec. Gen. Genet. vol. 168, pp. 111-115, 1979.

*Coombs, J., Dictionary of Biotechnology, Stockton Press, New York, N.Y., 1994.

*Contente et al., "Marker Rescue Transformation by Linear Plasmid DNA in Bacillus subtilis," Plasmid, vol. 2, pp. 555-571, 1979.

*Cristobal et al., "Competition between Sec- and TAT-dependent protein translocation in Escherichia coli, EMBO, vol. 18 pp. 2982-2990, 1999.

*Cserzo et al., "Prediction of transmembrane α-helices in prokaryotic membrane proteins: the dense alignment surface method," Protein Engin. vol. 10 pp. 673-676, 1997.

*Dalbey et al., "Protein translocation into and across the bacterial plasma membrane and the plant thylakoid membrane," TIBS, vol. 24, pp. 17-21, 1999.

*Database EMBL, Daniels D. L. et al., << Deoxyribonuclease tatD, >> Database accession No. P27859, XP002227139.

*Dieffenbach et al., PCR Primer, a Laboratory Manual, Cold Springs Harbor Press, Plainview, N.Y., 1995.

*Donovan et al., "Genes Encoding Spore Coat Polypeptides from Bacillus subtilis," J. Mol. Biol., vol. 196, pp. 1-10, 1987.

*Eder et al., "Bacillus subtilis secreted phosphodi esterase/alkaline phosphatase in the product of a Pho regulon gene, phoD," Microbiology, vol. 142, pp. 2041-2047, 1996.

*Eymann et al., "Phosphate-starvation-inducible proteins in Bacillus subtilis: a two-dimensional gel electrophoresis study," Microbiology, vol. 142, pp. 3163-3170, 1996.

*Fischer et al., "Introduction of plasmid pC194 into Bacillus thuringiensis by Protoplast transformation and plasmid transfer," Archives of Microbiology, vol. 139, pp. 213-217, 1984.

*Glover, D. M. (ed), DNA Cloning: A Practical Approach, MRL Press, Ltd., Oxford, U. K. vol. I, II.

*Grunstein et al., "Colony hybridization: A method for the isolation of cloned DNAs that contain a specific gene," Proc. Nat. Acad. Sci. USA, vol. 72, No. 10, pp. 3961-3965, Oct. 1975.

*Haima, Peter et al., "Novel plasmid marker rescue transformation system for molecular cloning in Bacillus subtilis enabling direct selection of recombinants," Mol. Gen. Genet. vol. 223, pp. 185-191, 1990.

*Hale & Marham, The Harper Collins Dictionary of Biology, Harper Perennial, NY (1991).

*Hampton, R. et al., Serological Methods, a Laboratory Manual, APS Press, St. Paul, MN. 1990.

*Harwood et al., Molecular Biological Methods for Bacillus, John Wiley & Sons, 1990.

*Hirose et al., "Proteome analysis of Bacillus subtilis extracellular proteins: a two-dimensional protein electrophoretic study," Microbiology, vol. 146, pp. 65-75, 2000.

*Holubova et al., "Transfer of Liposome-Encapsulated Plasmid DNA to Bacillus subtilis Protoplasts and Calcium-Treated Escherichia coli Cells," Folia Microbiol. vol. 30, pp. 97-100, 1985.

*Hulett et al., "Evidence for Two Structural Genes for Alkaline Phosphatase in Bacillus subtilis," J. Bacteriol. vol. 172, pp. 735-740, 1990.

*Hynds et al., "The Sec-independent Twin-arginine Translocation System Can Transport Both Tightly Folded and Malfolded Proteins across the Thylakoid Membrane," J. Biol. Chem. vol. 273, pp. 34868-3474, 1998.

*Jack et al., "Constitutive Expression of Escherichia coli tat Genes Indicates an Important Role for the Twin-Arginine Translocase during Aerobic and Anaerobic Growth," J. Bacteriology, vol. 183, pp. 1801-1804, 2001.

*Jongbloed, Jan D. H. et al., << TatC Is a Specificity Determinant for Protein Secretion via the Twin-arginine Translocation Pathway, >> Journal of Biological Chemistry, vol. 275, No. 52, pp. 41350-41357, Dec. 29, 2000.

*Keifer et al., "Negative charged amino acid residues play an active role in orienting the Sec-independent Pf3 coat protein in the Escherichia coli inner membrane," EMBO, vol. 16, pp. 2197-2204, 1997.

*Klenk et al., "The complete genome sequence of the hyperthermophilic, sulphate-reducing archaeon Archaeoglobus fulgidus," Nature, vol. 394, pp. 364-370, 1998.

*Kroll et al., "A Multifunctional Prokaryotic Protein Expression System: Overproduction, Affinity Purification, and Selective Detection," DNA and Cell Biology, vol. 12, No. 5, pp. 441-453, 1993.

*Kunst et al., "The complete genome sequence of the Gram-positive bacterium Bacillus subtilis," Nature, vol. 390, pp. 249-264, Nov. 20, 1997.

*Kyte et al., "A Simple Method for Displaying the Hydropathic Character of a Protein," J. Mol. Biol. vol. 157, pp. 105-132, 1982.

*Laemmli U. K. "Cleavage of Structural Proteins during the Assembly of the Head of Bacteriophage T4," Nature, vol. 227, pp. 680-685, 1970.

*Maddox et al., "Elevated Serum Levels in Human Pregnancy of a Molecule Immunochemically Similar to Eosinophil Granule Major Basic Protein," J. Exp. Med., vol. 158, pp. 1211-1226, Oct. 1983.

*Mann et al., "Transformation of Bacillus spp.: an Examination of the Transformation of Bacillus Protoplasts by Plasmids pUB110 and pHV33," Current Microbiology, vol. 13, pp. 191-195, 1986.

*McDonald et al., "Plasmid Transformation of Bacillus sphaericus 1593," Journal of General Microbiology, vol. 130, pp. 203-208, 1984.

*Miller, J. H., Experiments in Molecular Biology, Cold Spring Harbor Laboratory Press, Cold Spring Harbor NY (1982).

*Muller et al., "Suppression of the growth and export defects of an Escherichia coli secA(Ts) mutant by a gene cloned from Bacillus subtilis," Mol. Gen. Genet. vol. 235, pp. 98-96, 1992.

*Muller et al., "Localisation of the cell wall-associated phosphodiesterase PhoD of Bacillus subtilis," FEMS Micro. Letters, vol. 180, pp. 287-296, 1999.

*Muller et al., "Influence of Bacillus subtilis phoR on cell wall anionic polymers," Microbiology, vol. 143, pp. 947-956, 1997.

*Murray et al., "Codon usage in plant genes," Nucleic Acids Research, vol. 17, No. 2, pp. 477-498, 1989.

*Otto et al., "Identification of human myocardial proteins separated by two-dimensional electrophoresis using an effective sample preparation for mass spectrometry," Electrophoresis, vol. 17, pp. 1643-1650, 1996.

*Porath, Jerker, "Immobilized Metal Ion Affinity Chromatography," Protein Expression and Purification, vol. 3, pp. 263-281, 1992.

*Pragai et al., "The signal peptidase II (Isp) gene of Bacillus subtilis," Microbiology, vol. 143, pp. 1327-1333, 1997.

*Qi et al., "Role of PhpP~P in Transcriptional Regulation of Genes Involved in Cell Wall Anionic Polymer Biosynthesis in Bacillus subtilis," J. Barteriol. vol. 180, pp. 4007-4010, 1998.

*Rodrigue et al., "Co-translocation of a Periplasmic Enzyme Complex by a Hitchhiker Mechanism through the Bacterial Tat Pathway," J. Biol. Chem., vol. 274, pp. 13223-13228, 1999.

*Sambrook, J. et al., Molecular Cloning, A Laboratory Manual, 2nd Ed., Cold Spring Harbor Laboratory Press, Cold Spring Harbor, New York, 1989.

*Santini et al., "A novel Sec-independent periplsmic protein translocation pathway in Escherichia coli," EMBO, vol. 17, pp. 101-112, 1998.

*Sargent et al., "Overlapping functions of components of a bacterial Sec-independent protein export pathway," EMBO, vol. 17, pp. 3640-3650, 1998.

*Database EMBL, Sargent, F. et al., << TATB Protein, >> Database accession No. 069415, XP002133195.

*Sargent et al., "Sec-independent protein Translocation in *Escherichia coli*," J. Biol. Chem., vol. 274, pp. 36073-36082, 1999.
*Database EMBL, Sargent, F. et al., << Sec-Independent Protein Translocase Protein TATC, >> Database accession No. P27857, XP002133196.
*Schaeffer et al., "Catabolic Repression of Bacterial Sporulation," Proc. Natl. Acad. Sci. USA, vol. 54, pp. 704-711, 1965.
*Settles et al., "Sec-Independent Protein Translocation by the Maize Hc106 Protein," Science, vol. 278, pp. 1467-1470, 1997.
*Singleton et al., Dictionary of Microbiology and Molecular Biology, 2D Ed., John Wiley and Sons, New York (1994).
*Sipos et al., "Predicting the topology of eukaryotic membrane proteins," Eur. J. Biochem, vol. 213, pp. 1333-1340, 1993.
*Smith, Michael et al., "Protoplast Transformation in Coryneform Bacteria and Introduction of an α-Amylase Gene from *Bacillus amyloliquefaciens* into *Brevibacterium lactofermentum*," Applied and Environmental Microbiology, vol. 51, No. 3, pp. 634-639, Mar. 1986.
*Stanley et al., "*Escherichia coli* Strains Blocked in Tat-Dependent Protein Export Exhibit Pleiotropic Defects in the Cell Envelope," J. Bacteriol. vol. 183, pp. 139-144, 2001.
*Stephenson et al., "Influence if a Cell-Wall-Associated Protease on Production of α-Amylase by *Bacillus subtilis*," App. Environ. Microbiol. vol. 64, pp. 2875-2881, 1998.
*Thompson et al., "CLUSTAL W: improving the sensitivity of progressive multiple sequence alignment through sequence weighting, position-specific gap penalties and weight matrix choice," Nuc. Acids Res, vol. 22, pp. 4673-4680, 1994.
*Tjalsma et al., "Functional analysis of the secretory precursor processing machinery of *Bacillus subtilis*: identification of a eubacterial homolog of archaeal and eukaryotic signal peptidases," Genes & Develop. vol. 12, pp. 2318-2331, 1998.
*Tjalsma et al., "*Bacillus subtilis* Contains Four Closely Related Type I Signal Peptidases with Overlapping Substrate Specificities," J. Biol. Chem., vol. 272, pp. 25983-25992, 1997.
*Tjalsma et al., "The Role of Lipoprotein Processing by Signal Peptidase II in the Gram-positive Eubacterium *Bacillus subtilis*," J. Biol. Chem., vol. 274, pp. 1698-1707, 1999.
*Tjalsma, Harold et al., "Signal Peptide-Dependent Protein Transport in *Bacillus subtilis*: a Genome-Based Survey of the Secretome," *Microbiology and Molecular Biology*, vol. 64, No. 3, pp. 515-547, Sep. 2000.
*Towbin et al., "Electrophoretic transfer of proteins from polyacrylamide gels to nitrocellulose sheets: Procedure and some applications," Proc. Natl. Acad. Sci. USA, vol. 76, pp. 4350-4354, 1979.
*Vagner et al., "A vector for systematic gene inactivation in *Bacillus subtilis*," Microbiology, vol. 144, pp. 3097-3104, 1998.
*Van Dijl et al., "Non-functional expression of *Escherichia coli* signal peptidase I in *Bacillus subtilis*," J. Gen. Microbiology, vol. 137, pp. 2073-2083, 1991.
*Van Dijl et al., "Signal peptidase I overproduction results in increased efficiencies of export and maturation of hybrid secretory proteins in *Escherichia coli*," Mol. Gen. Genet, vol. 227, pp. 40-48, 1991.
*Van Dijl et al., "Identification of the Potential Active Site of the Signal Peptidase SipS of *Bacillus subtilis*," J. Biol. Chem., vol. 270, pp. 3611-3618, 1995.
*Van Dijl, Jan Maarten et al., << Functional genomic analysis of the *Bacillus subtilis* Tat Pathway for protein secretion, >> *Journal of Biotechnology*, pp. 243-254, Sep. 25, 2002.
*Vorobjeva et al., "Transformation of *Bacillus megaterium* Protoplasts by Plasmid DNA," FEMS Microbiology Letters 7, pp. 261-263, 1980.
*Weiner et al., "A Novel and Ubiquitous system for Membrane Targeting and Secretion of Cofactor-Containing Proteins," Cell, vol. 93, pp. 93-101, 1998.
*Weinrauch et al., "Plasmid Marker Rescue Transformation Proceeds by Breakage-Reunion in *Bacillus subtilis*," Journal of Bacteriology, vol. 169, No. 3, pp. 1205-1211, Mar. 1987.
*Weinrauch et al., "Plasmid Marker Rescue Transformation in *Bacillus subtilis*," Journal of Bacteriology, vol. 154, No. 3, pp. 1077-1087, Jun. 1983.
*Wu et al., "Bacterial Twin-Arginine Signal Peptide-Dependent Protein Translocation Pathway: Evolution and Mechanism," J. Mol. Microbiol. Biotechnol. vol. 2, pp. 179-189, 2000.
*Yu et al., "The Cytochrome bc Complex (menaquinone: Cytochrome c Reductase) in *Bacillus subtilis* Has a Nontraditional Subunit Organization," J. Bacteriol. vol. 177, pp. 6751-6760, 1995.

* cited by examiner

```
TatA(Eco)   M-GGISIWQLLIIAVIVVLLFGTKKLG--------------------------  26
TatE(Eco)   M-GEISITKLLVVAALVVLLFGTKKLR--------------------------  26
TatAy(Bsu)  M--PIGPGSLAVIAIVALIIFGPKKLP--------------------------  25
TatAd(Bsu)  MFSNIGIPGLILIFVIAIIIFGPSKLP--------------------------  27
TatAc(Bsu)  M--ELSFTKILVILFVGFLVFGPDKLP--------------------------  25
TatB (Eco)  MFDIGFSELLLVFIIGLVVLGPQRLPVAVKTVAGWIRALRSLATTVQNELTQELKLQ 49
              *   ..   ...  . ...*. .*

TatA(Eco)   ---------------SIGSDLGASIKGFKKAMSDDE----PKQDKTSQDADFTAKTI  64
TatE(Eco)   ---------------TLGGDLGAAIKGFKKAMNDDD----A-AAKKGADVDLQAEKL  63
TatAy(Bsu)  ---------------ELGKAAGDTLREFKNATKGLT----SDEEEKKKEDQ------  57
TatAd(Bsu)  ---------------EIGRAAKRTLLEFKSATKSLV----SGDEKEEKSAELTAVK-  64
TatAc(Bsu)  ---------------ALGRAAGKALSEFKQATSGLT----QDIRKNDSEN-----K-  57
TatB (Eco)  EFQDSLKKVEKASLTNLTPELKASMDELRQAAESMKRSYVANDPEKASDEAHTIHNP  114
                ... .    .. ...  *  ..         ..  .

TatA(Eco)   ADKQADTNQE--------------------------------QAKTEDAKRHDKEQV  89
TatE(Eco)   SHKE--------------------------------------                67
TatAy(Bsu)  ------------------------------------------                57
TatAd(Bsu)  ------------------------------------------QDKNAG         70
TatAc(Bsu)  ------------------------------------------EDKQM-         62
TatB (Eco)  VVKDNEAAHEGVTPAAAQTQASSPEQKPETTPEPVVKPAADAEPKTAAPSPSSSDKP 171
```

FIG._1A

```
TatC (Eco)  MSVEDTQ--PLITHLIELRKRLLNCIIAVIVIFLCLVYFANDIYH-LVSAPLIK   51
TatCy(Bsu)  MTRMKVNQMSLLEHIAELRKRLLIVALAFVVFFIAGFFLAKPIIVYLQETDEAK   50
TatCd(Bsu)  MDKKETH---LIGHLEELRRRIIVTLAAFFLFLITAFLFVQDIYDWLIRDLDGK   51
             *.   ...  *..*. ***.*..    *  ....   ...*  *   .    *

TatC (Eco)  QLPQGSTMIATDVASPFFTPIKLTFMVSLILSAPVILYQVWAFIAPALYKHERR   105
TatCy(Bsu)  QL----TLNAFNLTDPLYVMQFAFIIGIVLTSPVILYQLWAFVSPGLYEKERK   104
TatCd(Bsu)  ------LAVLGPSEILWVYMMLSGICAIAASIPVAAYQLWRFVAPALTKTERK    98
              . .    ...  ...    ... .     . **  **.* *..*.* . **

TatC (Eco)  LVVPLLV---SSSLLFYIGMAFAYFVVFPLAFGFLANTAPE-GVQVSTDIASYL   155
TatCy(Bsu)  VTLSYI---PVSILLFLAGLSFSYYILFPFVVDFMKRISQDLNVNQVIGINEYF   155
TatCd(Bsu)  VTIMYIMYIPGLFALFLAGISFGYFVLFPIVLSFLTHLSSG-HFETMFTADRYF   151
             ...  .      **  *...*...**. .*. .. . . .           *.

TatC (Eco)  SFVMALFMAFGVSFEVPVAIVLLCWMGITSPEDLRKKRPYVLVGAFVVGMLLTP   209
TatCy(Bsu)  HFLLQLTIPFGLLFQMPVILMFLTRLGIVTPMFLAKIRKYAYFTLLVIAALITP   209
TatCd(Bsu)  RFMVNLSLPFGFLFEMPLVVMFLTRLGILNPYRLAKARKLSYFLLIVVSILITP   205
             *...*  ..** ..*.*  ...** .**  .*  .* * *  .*..  *.**

TatC (Eco)  PDVFSQTLLAIPMYCLFEIGVFFSRF-YVGKGRNREEENDAEAESEKTEE   258
TatCy(Bsu)  PELLSHMMVTVPLLILYEISILISKAAYRKAQKSSAADRDVSSG-----Q   254
TatCd(Bsu)  PDFISDFLVMIPLLVLFEVSVTLSAFVYKKRMRE-----ETAAA-----A   245
             *..*. .. .*.  .*.*... .  *     ..          .
```

FIG._1B

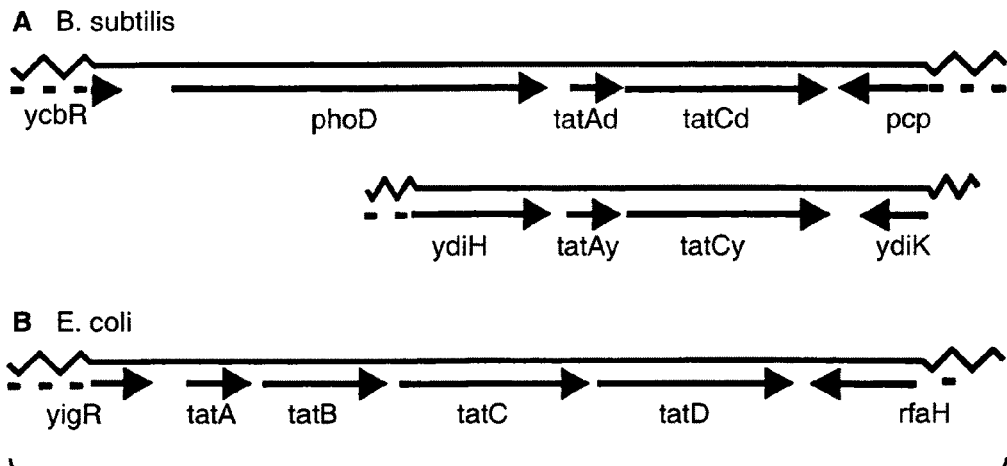
FIG._2
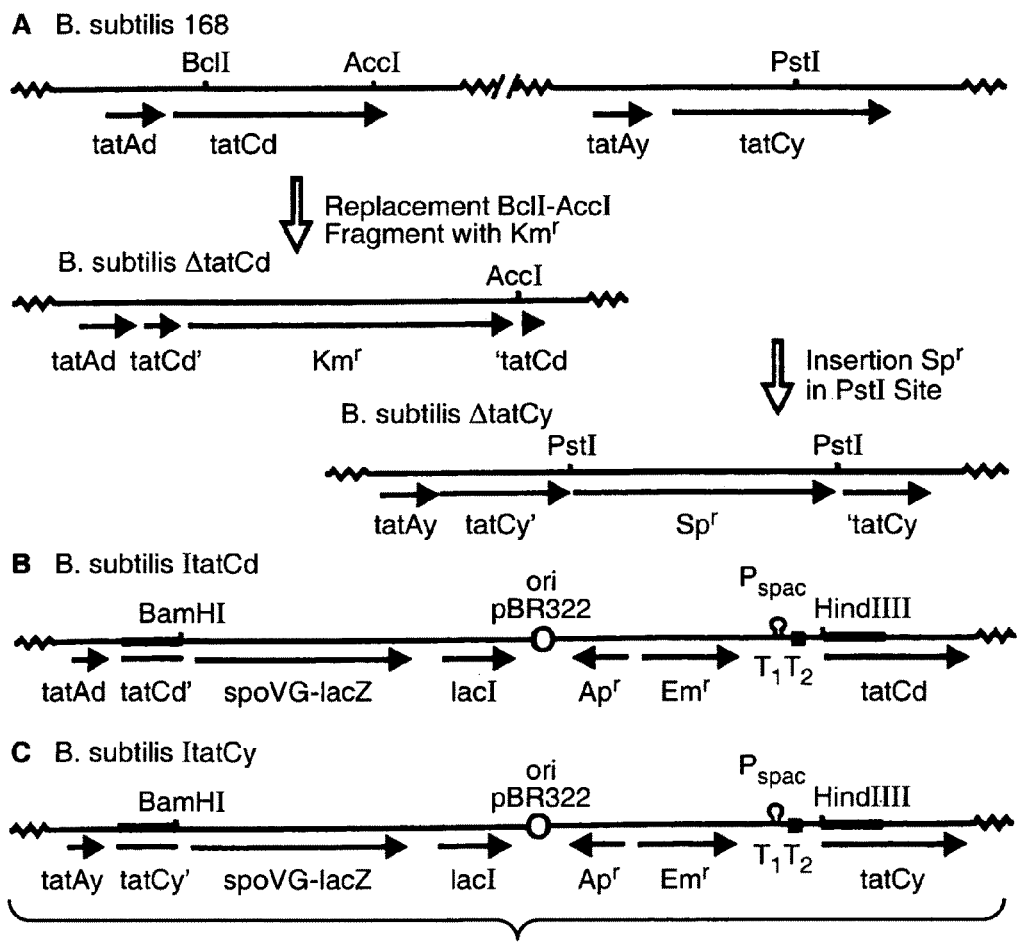
FIG._3

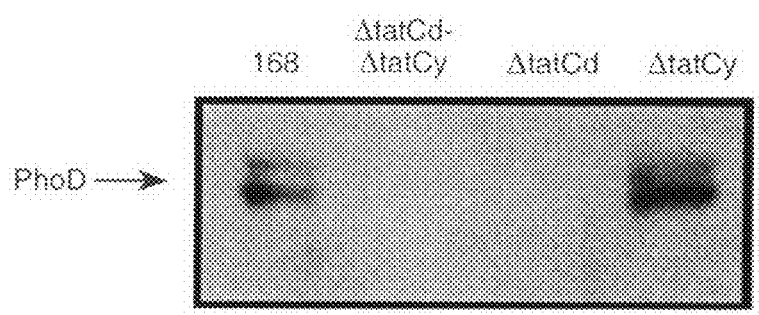
*FIG._4A*
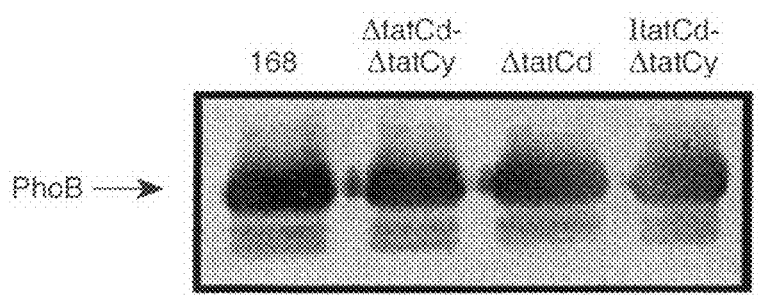
*FIG._4B*
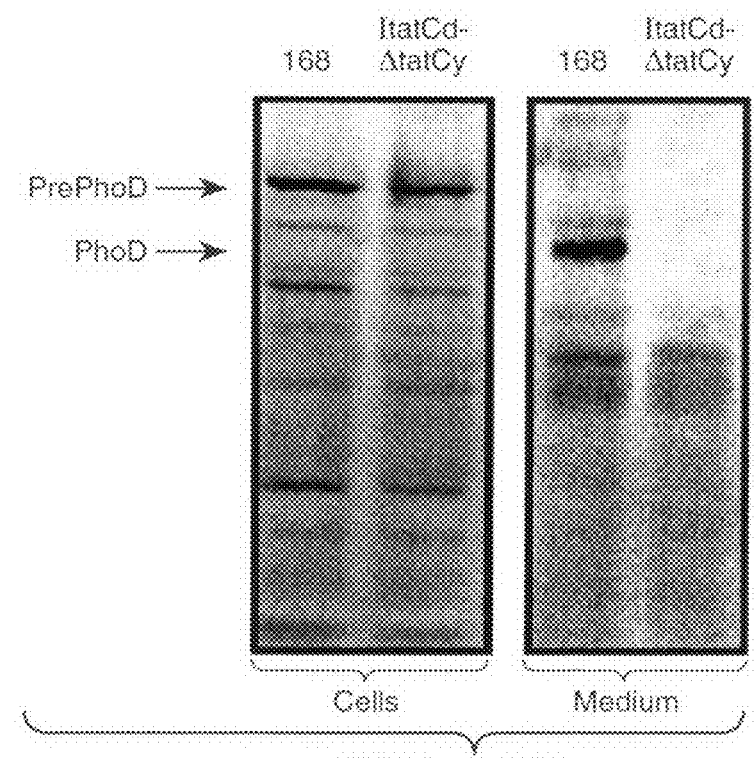
*FIG._4C*

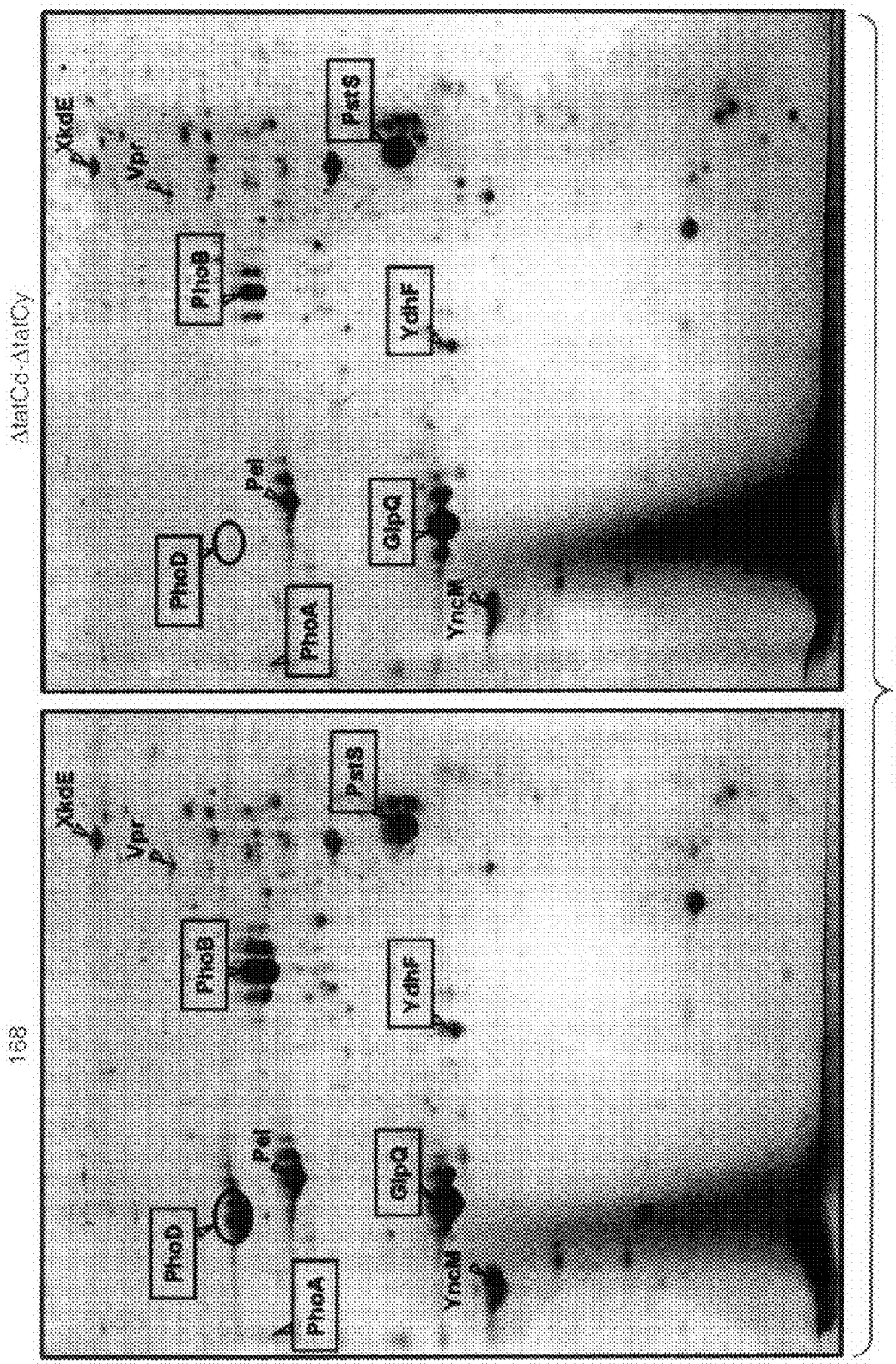
FIG._5

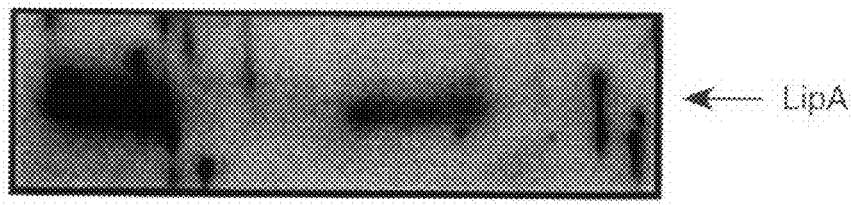
FIG._6
| Protein | N | h | RR-Motif | H | h | C |
|---|---|---|---|---|---|---|
| AlbB | 1 | 0.1 | RRILL | 27 | 2.0 | AIA |
| AmyX ᵀᴹ | 9 | -0.8 | RRSFE | 15 | 1.1 | - |
| AppB ᵀᴹ | 8 | 0.5 | RRTLM | 19 | 2.3 | - |
| LipA | 7 | -1.1 | RRIIA | 19 | 1.2 | AKA |
| OppB ᵀᴹ | 8 | -0.6 | RRLVY | 24 | 2.0 | - |
| PbpX | 2 | -2.2 | RRRKL | 14 | 2.9 | WNA |
| PhoD | 3 | -1.3 | RRKFI | 17 | 0.9 | VGA |
| QcrA ᵀᴹ | 1 | -1.1 | RRQFL | 19 | 1.3 | - |
| TlpA ᵀᴹ | 1 | -0.8 | RRLII | 21 | 2.4 | - |
| WapA ᵂ | 1 | -3.0 | RRNFK | 18 | 2.3 | VLA |
| WprA | 8 | -1.7 | RRKFS | 20 | 1.9 | AAA |
| YceA ᵀᴹ | 1 | -0.4 | RRAFL | 21 | 2.2 | - |
| YesM ᵀᴹ | 1 | -1.5 | RRMKI | 20 | 2.4 | QYA |
| YesW | 1 | -1.3 | RRSCL | 19 | 2.0 | VKA |
| YfkN ᵀᴹ | 1 | -1.2 | RRTHV | 17 | 1.7 | IHA |
| YkpC | 8 | -1.0 | RRVAI | 17 | 2.3 | SLA |
| YkuE | 1 | -1.3 | RRQFL | 17 | 1.0 | GYA |
| YmaC | 7 | 0.0 | RRFLL | 15 | 2.4 | YSL |
| YubF ᵀᴹ | 9 | -2.7 | RRNTV | 23 | 2.0 | - |
| YuiC | 8 | 0.2 | RRLLM | 20 | 1.9 | IEA |
| YvhJ ᵀᴹ | 2 | -1.7 | RRKIL | 18 | 2.5 | - |
| YwbN | 1 | -1.8 | RRDIL | 23 | 1.4 | QTA |
FIG._7

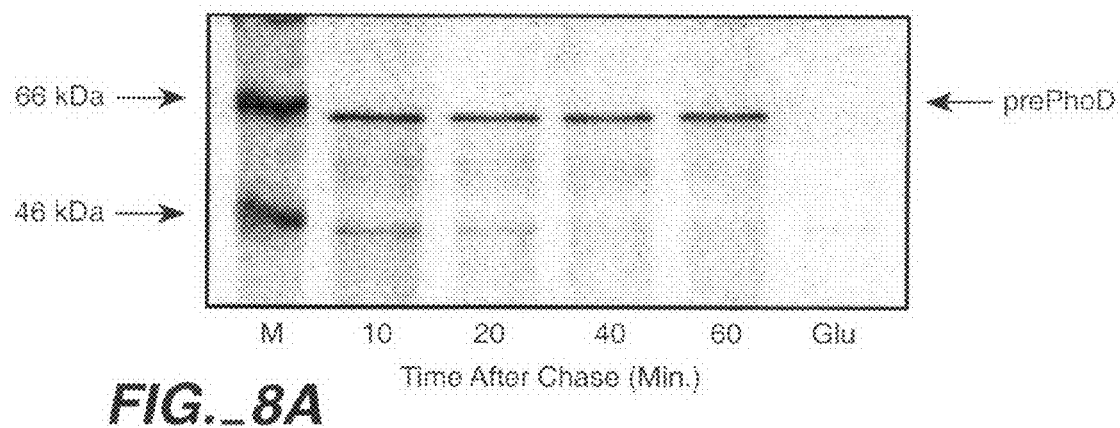
FIG._8A
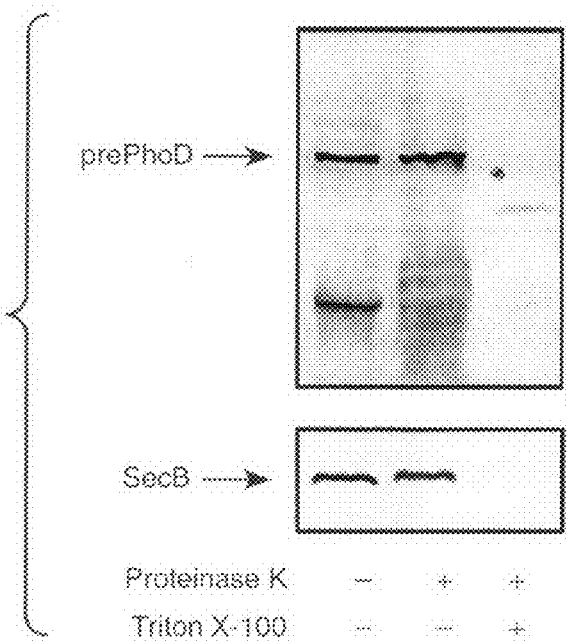
FIG._8B

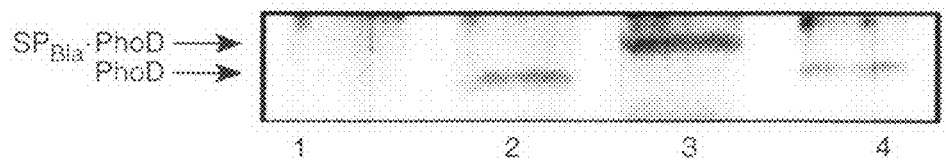
FIG._9A
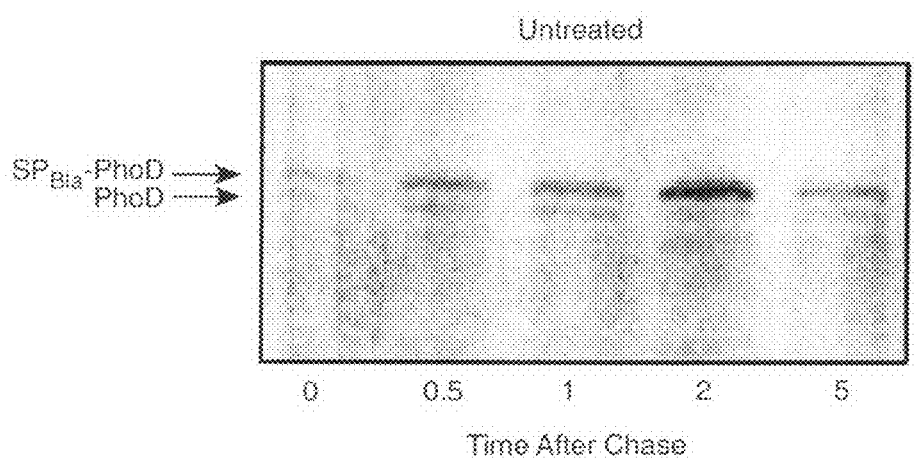
FIG._9B
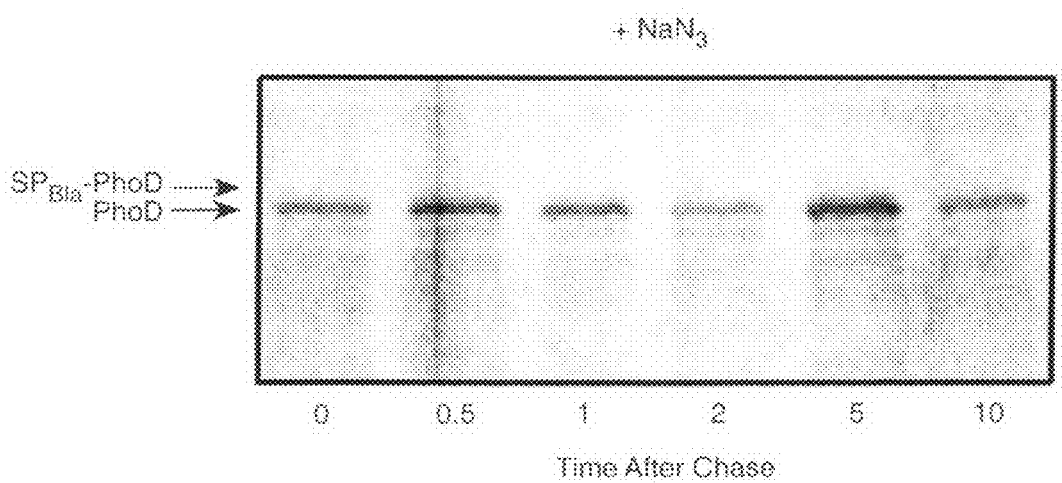
FIG._9C

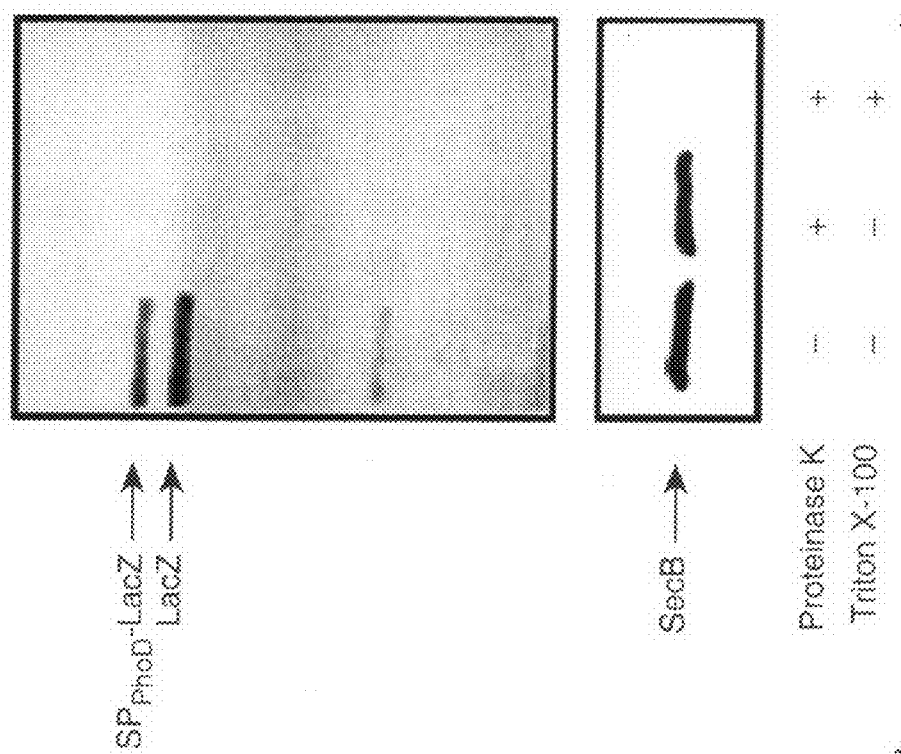
FIG._10B
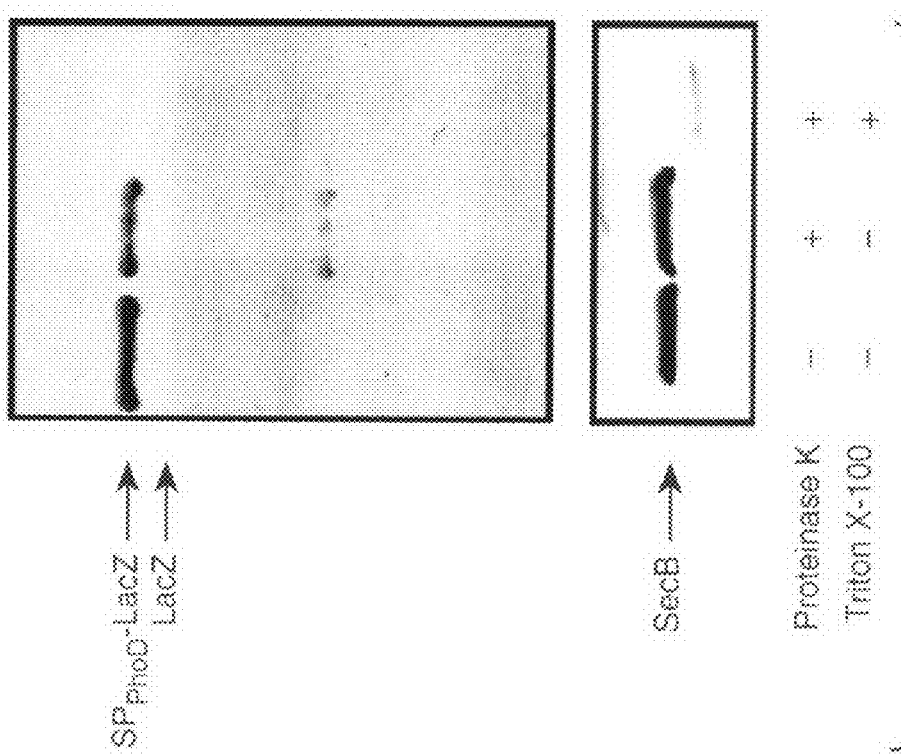
FIG._10A

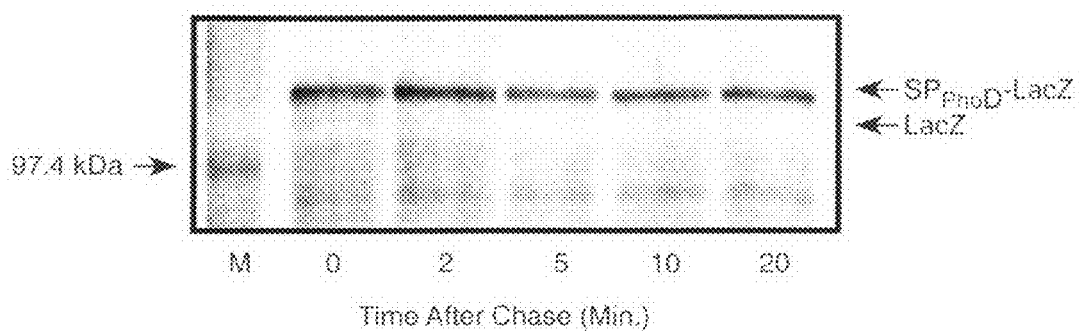
FIG._11A
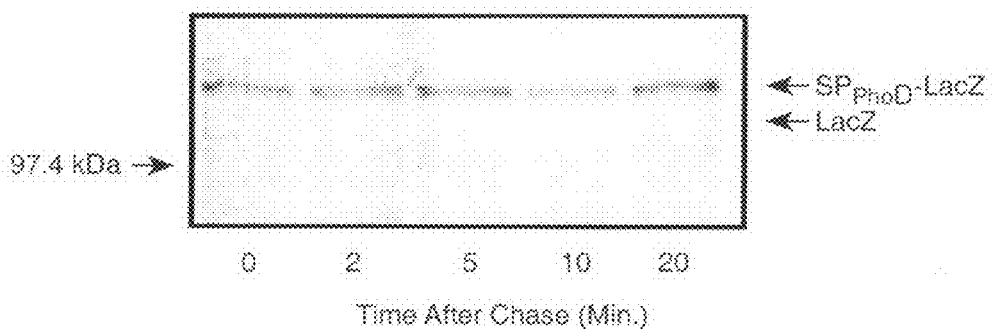
FIG._11B

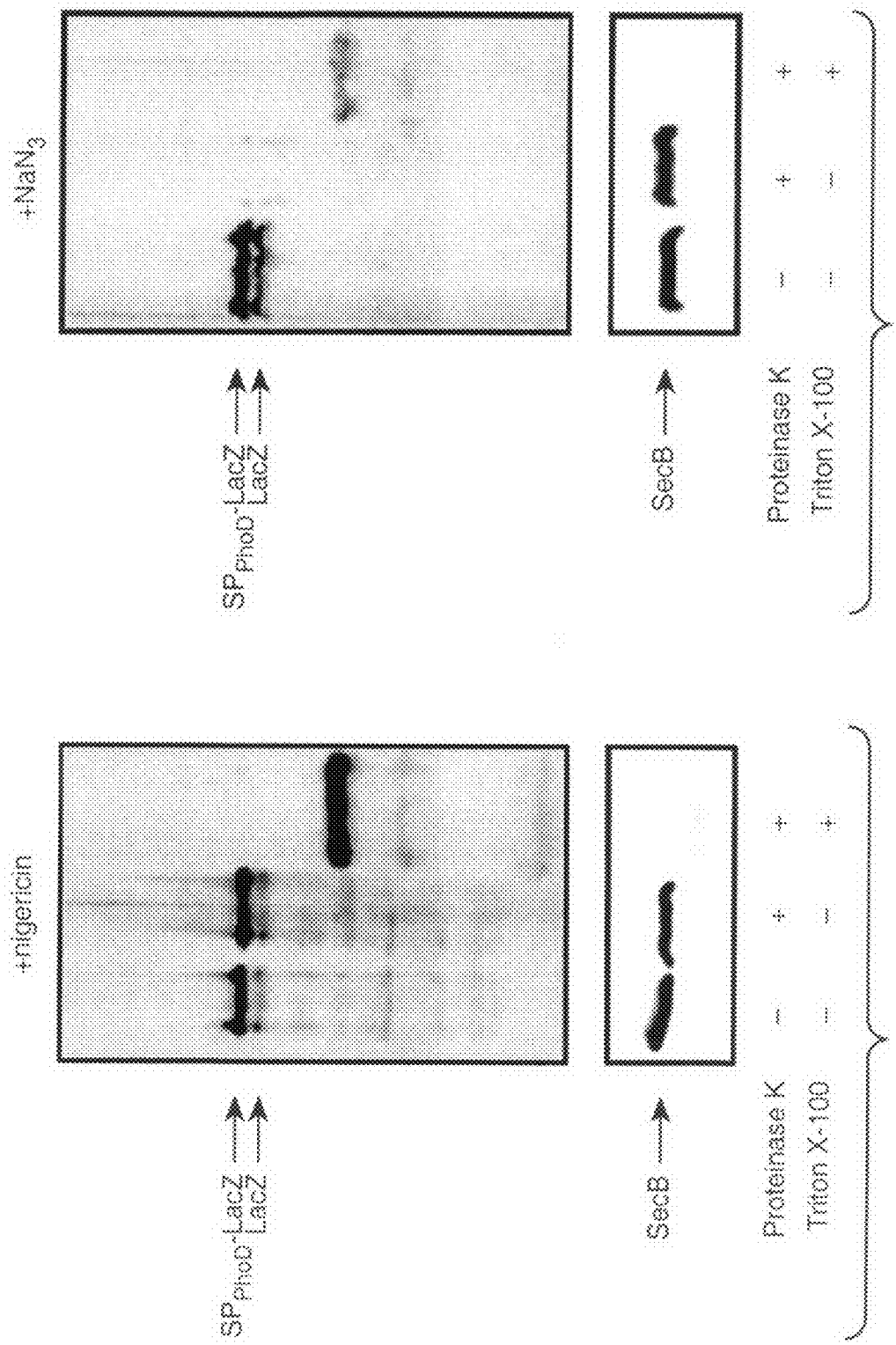

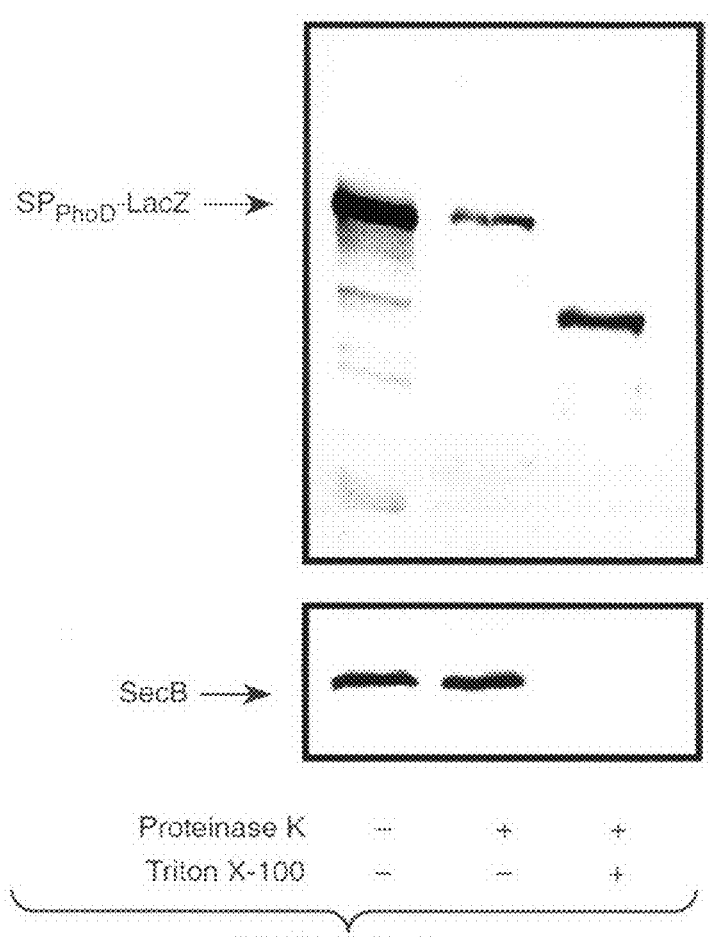

FIG._13

Homologs in B. alcalophilus

TatA
MGGLSVGSVVLIALVALLIFGPKKLPELGKAAGSTLREFKNATK
GLADDDDDTKSTNVQKEKA

TatC
MTMMTPNQQTSKKKKRKGRKGRVPMQDMSIMDHAEELRRRIF
VVLAFFIVALIGGFFLAVPVITFLQNSPQAADMPFNAFRLTDPLRV
YMNFAVITALVLIIPVILYQLWAFVSPGLKENEQKATLAYIPIAFL
LFLAGIAFSYFILLPFVISFMGQMADRLEINEMYGINEYFSFLFQL
TIPFGLLFQLPVVVMFLTRLGVVTPTFLRKIRKYAYFALLVIAGII
TPPELTSHLFVTVPMLILYEISITISAITYRKYHGTTDHNGQESAK

FIG._14

TWIN-ARGININE TRANSLOCATION IN BACILLUS

CROSS-REFERENCE TO RELATED APPLICATIONS

This is a divisional of Ser. No. 09/954,737, now U.S. Pat. No. 7,316,924, filed on Sep. 17, 2001, which application claims benefit of and priority to U.S. Application No. 60/233,610, entitled "Twin-Arginine Translocation in *Bacillus*", filed Sep. 18, 2000 by Jongbloed et al.

FIELD OF THE INVENTION

The present invention generally relates to expression of proteins in a host cell. The present invention provides expression vectors, methods and systems for the production of proteins in a host cell.

BACKGROUND OF THE INVENTION

Eubacteria export numerous proteins across the plasma membrane into either the periplasmic space (Gram-negative species), or the growth medium (Gram-positive species). The Gram-positive eubacterium *Bacillus subtilis* and, in particular, its close relatives *Bacillus amyloliquefaciens* and *Bacillus licheniformis* are well known for their high capacity to secrete proteins (at gram per liter concentrations) into the medium. This property, which allows the efficient separation of (secreted) proteins from the bulk cytoplasmic protein complement, has led to the commercial exploitation of the latter bacilli as important "cell factories." Despite their high capacity to secrete proteins of Gram-positive origin, the secretion of recombinant proteins from Gram-negative eubacterial or eukaryotic origin by *Bacillus* species is often inefficient. This can be due to a variety of (potential) bottlenecks in the secretion pathway, such as poor targeting to the membrane, pre-translocational folding, inefficient translocation, slow or incorrect post-translocational folding of the secretory protein, and proteolysis. Notably, many of these problems relate to the specific properties of the general secretory (Sec) pathway that was, so far, used in all documented attempts to apply bacilli for the secretion of heterologous proteins of commercial or biomedical value.

General strategies for the secretion of heterologous proteins by bacilli are based on the in-frame fusion of the respective protein with an amino-terminal signal peptide that directs this protein into the Sec-dependent secretion pathway. Upon translocation across the membrane, the signal peptide is removed by a signal peptidase, which is a prerequisite for the release of the translocated protein from the membrane, and its secretion into the medium. As exemplified with human interleukin-3, which is secreted by *B. licheniformis* at gram per liter concentrations, this strategy allows protein production at commercially significant levels.

Two major hurdles have been identified for the secretion of heterologous proteins via the Sec-dependent route. The first one is the translocation process by the Sec machinery, which is composed of a proteinaceous channel in the membrane (consisting of SecY, SecE, SecG and SecDF-YrbF) and a translocation motor (SecA). The Sec machinery is known to thread its substrates in an unfolded state through the membrane. Consequently, this machinery is inherently incapable of translocating proteins that fold in the cytosol. A second bottleneck has been identified for other heterologous proteins that are translocated correctly but fold slowly or incorrectly in the cell wall environment, probably because this compartment lacks the appropriate chaperone molecules to assist in their folding. Molecular chaperones of the Hsp60 and Hsp70 classes are essential for the folding of many proteins, but these are all absent from bacterial extracytoplasmic compartments. As the membrane-cell wall environment of bacilli is highly proteolytic, slowly or incorrectly folding translocated proteins are often degraded before being secreted into the medium. Consequently, protein secretion via the Sec pathway is a highly efficient tool for the production of only a subset of heterologous proteins.

Protein production and secretion from *Bacillus* species is a major production tool with a market of over $1 billion per year. However, as noted above, the standard export technologies, based on the well-characterized general secretory (Sec) pathway, are frequently inapplicable for the production of proteins. Thus, it would be beneficial to have an alternative mechanism for the production and secretion proteins.

SUMMARY OF THE INVENTION

Provided herein are methods for the production of peptides in a host cell.

In one aspect of the invention, the host cell is a gram-positive micro-organism. The gram-positive microorganism is preferably a member of the genus *Bacillus*. In a more preferred embodiment the host cell is *Bacillus subtilis*.

In another aspect of the invention, the host cell is a gram-negative micro-organism. The gram-negative microorganism is preferably a member of the genus *Pantoea*, preferably *Pantoea citrea*. The gram-negative microorganism is preferably *Escherichia coli*.

The present invention also provides methods for increasing secretion of proteins from host microorganisms. In one embodiment of the present invention, the protein is homologous or naturally occurring in the host microorganism. In another embodiment of the present invention, the protein is heterologous to the host microorganism. Accordingly, the present invention provides a method for increasing secretion of a protein in a host cell using an expression vector comprising nucleic acid tatCd wherein said tatCd is under the control of expression signals capable of expressing said secretion factor in a host microorganism; introducing the expression vector into a host microorganism capable of expressing said protein and culturing said microorganism under conditions suitable for expression of said secretion factor and secretion of said protein.

The present invention provides expression vectors and host cells comprising a nucleic acid encoding a TatCd and/or TatA. In one embodiment of the present invention, the host cell is genetically engineered to produce a desired protein, such as an enzyme, growth factor or hormone. In yet another embodiment of the present invention, the enzyme is selected from the group consisting of proteases, carbohydrases including amylases, cellulases, xylanases, and lipases; isomerases such as racemases, epimerases, tautomerases, or mutases; transferases, kinases and phophatases acylases, amidases, esterases, oxidases. In a further embodiment the expression of the secretion factor TatCd is coordinated with the expression of other components of the secretion machinery. Preferably other components of the secretion machinery, i.e., TatA and/or other secretion factors identified in the future are modulated in expression at an optimal ratio to TatCd. For example, it may be desired to overexpress multiple secretion factors in addition TatCd for optimum enhancement of the secretion machinery.

The present invention also provides a method of identifying homologous gram positive microorganism TatCd that comprises hybridizing part or all of B. subtilis TatCd nucleic acid shown in FIG. 1 with nucleic acid derived from gram-positive microorganisms. In one embodiment, the nucleic acid is of genomic origin. In another embodiment, the nucleic acid is a cDNA. The present invention encompasses novel gram-positive microorganism secretion factors identified by this method.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE FIGURES

FIG. 1. Tat components of B. subtilis and E. coli. The amino acid sequences of Tat components of B. subtilis and E. coli as deduced from the SubtiList (http://bioweb.pasteur.fr/Genolist/SubtiList.html) and Colibri (http://bioweb.pasteur.fr/Genolist/Colibri.html) databases were used for comparisons. Identical amino acids [*], or conservative replacements [.] are marked. Putative transmembrane segments, indicated in gray shading, were predicted with the TopPred2 algorithm (34, 35) (A) Comparison of TatAc (YnzA), TatAd (YczB) and TatAy (YdiI) of B. subtilis (Bsu) with TatA, TatB and TatE of E. coli (Eco). (B) Comparison of TatCd (YcbT) and TatCy (YdiJ) of B. subtilis with TatC of E. coli.

FIG. 2. The tatAC regions of B. subtilis and E. coli. (A) Chromosomal organization of the B. subtilis tatAd-tatCd and tatAy-tatCy regions (adapted from the SubtiList database). Note that the tatAd and tatCd genes are located downstream of the phoD gene. (B) Chromosomal organization of the E. coli tatABCD region (adapted from the Colibri database).

FIG. 3. Construction of tatC mutant strains of B. subtilis. (A) Schematic presentation of the construction of B. subtilis ΔtatCd and B. subtilis ΔtatCy. The chromosomal tatCd gene was disrupted with a kanamycin resistance marker (Km$^r$) by homologous recombination. To this purpose, B. subtilis 168 was transformed with plasmid pJCd2, which cannot replicate in B. subtilis, and contains a mutant copy of the tatCd gene with an internal BclI-AccI fragment replaced by a Km$^r$ marker. The chromosomal tatCy gene was disrupted with a spectinomycin resistance marker (Sp$^r$) by homologous recombination. To this purpose, B. subtilis 168 was transformed with plasmid pJCy2, which cannot replicate in B. subtilis, and contains a mutant copy of the tatCy gene with a Sp$^r$ marker in the PstI site. Only restriction sites relevant for the construction are shown. tatCd', 5' end of the tatCd gene; 'tatCd, 3' end of the tatCd gene; tatCy', 5' end of the tatCy gene; 'tatCy, 3' end of the tatCy gene. (B) Schematic presentation of the tatCd region of B. subtilis ItatCd. By a Campbell-type integration of the pMutin2-derivative pMICd1 into the B. subtilis 168 chromosome, the tatCd gene was placed under the control of the IPTG-dependent Pspac promoter, which can be repressed by the product of the lacI gene. Simultaneously, the spoVG-lacZ reporter gene of pMutin2 was placed under the transcriptional control of the tatCd promoter region. PCR-amplified regions are indicated with black bars. Ori pBR322, replication functions of pBR322; Ap$^r$, ampicillin resistance marker; Em$^r$, erythromycin resistance marker; tatCd', 3' truncated tatCdgene; T1T2, transcriptional terminators on pMutin2. (C) Schematic presentation of the tatCy region of B. subtilis ItatCy. By a Campbell-type integration of the pMutin2-derivative pMICy1 into the B. subtilis 168 chromosome, the tatCy gene was placed under the control of the IPTG-dependent Pspac promoter. Simultaneously, the spoVG-lacZ reporter gene of pMutin2 was placed under the transcriptional control of the tatCy promoter region. tatCy', 3' truncated tatCy gene.

FIG. 4. TatCd is required for secretion of PhoD. B. subtilis 168 (parental strain), B. subtilis ΔtatCd, B. subtilis ΔtatCy, or B. subtilis ΔtatCd-ΔtatCy were grown under conditions of phosphate starvation, using LPDM medium. To study the secretion of PhoD (A) or PhoB (B), B. subtilis cells were separated from the growth medium by centrifugation. Secreted PhoD and PhoB in the growth medium were visualized by SDS-PAGE and Western blotting, using PhoD- or PhoB-specific antibodies. (C) Cells of B. subtilis 168 and B. subtilis ItatCd-ΔtatCy were grown under conditions of phosphate starvation, in LPDM medium. Next, cells and growth medium were separated by centrifugation, and PhoD was visualised by SDS-PAGE and Western blotting, using PhoD-specific antibodies.

FIG. 5. Two-dimensional gel electrophoretic analysis of the TatC-dependent secretion of PhoD. B. subtilis 168 or B. subtilis ΔtatCd-ΔtatCy, were grown under conditions of phosphate starvation in LPDM medium. Secreted proteins were analysed by two-dimensional gel electrophoresis as indicated in the Experimental Procedures section. The names of proteins identified by mass spectrometry are indicated.

FIG. 6. TatC-dependent secretion of the B. subtilis lipase LipA. B. subtilis 168 (parental strain), B. subtilis ΔtatCd, B. subtilis ΔtatCy, or B. subtilis ΔtatCd-ΔtatCy were grown in TY-medium to end-exponential growth phase. To study the secretion of LipA, B. subtilis cells were separated from the growth medium by centrifugation. Proteins in the growth medium were concentrated 20-fold upon precipitation with trichloroacetic acid, and samples for polyacrylamide gel electrophoresis (SDS-PAGE) were prepared. Secreted LipA in the growth medium was visualized by SDS-PAGE and Western blotting, using LipA-specific antibodies.

FIG. 7. Predicted twin-arginine (RR-)signal peptides of B. subtilis. The listed signal peptides contain, in addition to the twin-arginines, at least one other residue of the consensus sequence (R-R-X-$\tilde{\phi}\phi$; printed in bold). The number of residues in the N- and H-domains of each signal peptide, and the average hydrophobicity (h) of each of these domains, as determined by the algorithms of Kyte and Doolittle (Kyte, J., and R. F. Doolittle [1982] A simple method for displaying the hydropathic character of a protein. J. Mol. Biol. 157:105-32), are indicated. Furthermore, the RR-motifs in the N-domain, and SPase I recognition sites in the C-domain (ie. positions –3 to –1 relative to the predicted SPase cleavage site) are shown. Proteins lacking a (putative) SPase I cleavage site, some of which contain additional transmembrane domains, are indicated with "$^{TM}$". One protein containing cell wall binding repeats is indicated with "$^W$".

FIG. 8. Processing of prePhoD in E. coli TG1. (A) E. coli TG11 carrying plasmid pARphoD, encoding wild type PhoD was grown in M9 minimal medium to early logarithmic phase. 1 hour prior labelling expression of phoD was induced with IPTG (1 mM). Cells were labelled for 1 min with [35S]-methionine, after which non-radioactive methionine was added. Samples were withdrawn at chase times 10, 20, 40 and 60 min and subjected to immunoprecipitation with monospecific antibodies against PhoD, followed by SDS-PAGE using a 10% polyacrylamide gel and fluorography. M, molecular weight marker; Glu, uninduced control. (B) In vivo protease mapping of PhoD in E. coli TG1 (pAR3phoD). Cells were converted to spheroplasts and treated with proteinase K, proteinase K and Trition X-100 or remained untreated as indicated. Localisation of prePhoD is indicated. Accessibility of proteinase K to the cytosol was analysed by monitoring SeeB in a 15% polyacrylamide gel. PhoD and SecB were detected by monospecific antibodies.

FIG. 9. Induction and processing Of $SP_{Bla}$-PhoD in *E. coli* TG1. (A) *E. coli* TG1 (pMUTIN2bla-phoD) was grown in TY medium to logarithmic growth phase. Expression of bla-phoD was induced with IPTG (1 mM, lanes 2-4) or remained uninduced (lane 1). At the time of induction cultures were treated with sodium azide (3 mM, lane 3), with nigericin (1 µM, lane 4) or remained untreated (lane 2). Samples were taken 20 min after induction of $SP_{Bla}$-PhoD, lysed and cell extracts were analysed by SDS-PAGE using 10% polyacrylamide. B and C, TG1 (pMUTIN2bla-phoD) was grown in M9 minimal medium to early logarithmic phase. 1 hour prior labelling expression of phoD was induced with IPTG (1 mM). While one culture remained untreated (B), the other was treated with sodium azide (3 mM) upon induction (C). Cells were labelled for 1 min with [35S]-methionine, after which non-radioactive methionine was added. Samples were withdrawn at times after chase as indicated in the figures and subjected to immunoprecipitation with antibodies against PhoD, followed by SDS-PAGE using a 12.5% polyacrylamide gel and fluorography. Localisation of $SP_{Bla}$-PhoD and mature PhoD is indicated. [14C]-labelled molecular weight marker.

FIG. 10. Localisation of $SP_{PhoD}$-LacZ in *E. coli* TG1 in absence or presence of *B. subtilis* tatAd/Cd. *E. coli* TG1 strains carrying either plasmid pAR3phoD-lacZ (A) or plasmids pAR3phoD-lacZ, pREP4 and pQE9tatAd/Cd (B) were grown in TY medium to exponential growth and expression of phoD-lacZ and tatAd/Cd were induced for 1 hour with arabinose (0.2%) and IPTG (1 mM), respectively. Subcellular localisation of $SP_{PhoD}$-LacZ was detected by in vivo protease mapping according to FIG. 8B. $SP_{PhoD}$-LacZ and SecB were monitored by antisera against LacZ and SecB. Bands representing $SP_{PhoD}$-LacZ, LacZ and SecB are indicated.

FIG. 11. Processing of $SP_{PhoD}$-LacZ in *E. coli* TG1 co-expressing *B. subtilis* tatAd/Cd. *E. coli* strains TG1 (pAFR3phoD-lacZ) (A) and TG1 (pAR3phoD-lacZ, pREP4, pQE9tatAd/Cd) (B) were grown in M9 minimal medium to early logarithmic phase and labelled for 1 min With [35S]-methionine and subsequently chased with non-radioactive methionine. Samples were taken at the indicated chase times and further processed by immunoprecipitation with antiserum against LacZ, followed by SDS-PAGE using a 7.5% polyacrylamide gel and fluorography. Bands representing $SP_{PhoD}$-LacZ and LacZ are indicated. M, [14C]-labelled molecular weight marker.

FIG. 12 TatAd/Cd-mediated transport of $SP_{PhoD}$-LacZ in *E. coli* is ΔpH-dependent. *E. coli* TG1 (pAR3phoD-lacZ, pREP4, pQE9tatAd/Cd) was grown in TY medium to exponential growth, nigericin (1 uM) (A) or sodium azide (3 mM) (B) were added to the cultures prior induction of gene expression. Localisation of LacZ was analysed by in vivo protease mapping as described in FIG. 10. Samples were submitted to immunological detection of LacZ with specific antibodies. Bands representing $SP_{PhoD}$-LacZ, LacZ and SecB are indicated.

FIG. 13 Localisation of $SP_{PhoD}$-LacZ in *E. coli* strain depleted for tatABCDE. *E. coli* strain TG1Δtat, 4BCDE (pAR3phoD-lacZ, pREP4 and pQE9tatAd/Cd) was grown in TY medium, synthesis of $SP_{PhoD}$-LacZ and TatAd/Cd were induced and subjected to in vivo protease mapping as described in FIG. 10. LacZ and SecB were visualised by SDS-PAGE and Western blotting, FIG. 14 Homologs of *B. clausii*. *B subtilis* sequences were used to BLAST search an in-house database of *B. clausii* genome.

DETAILED DESCRIPTION OF THE INVENTION

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

As used herein, the genus *Bacillus* includes all members known to those of skill in the art, including but not limited to *B. subtilis, B. licheniformis, B. lentus, B. brevis, B. stearothermophilus, B. alkalophilus, B. amyloliquefaciens, B. clausii, B. coagulans, B. circulans, B. lautus* and *B. thuringiensis*.

The term "polypeptide" as used herein refers to a compound made up of a single chain of amino acid residues linked by peptide bonds. The term "protein" as used herein may be synonymous with the term "polypeptide" or may refer, in addition, to a complex of two or more polypeptides.

The term "chimeric polypeptide" and "fusion polypeptide" are used interchangeably herein and refer to a signal peptide from phoD or lipA linked to the protein of interest or heterologous protein.

A "signal peptide" as used herein refers to an amino-terminal extension on a protein to be secreted. Nearly all secreted proteins use an amino-terminal protein extension which plays a crucial role in the targeting to and translocation of precursor proteins across the membrane and which is proteolytically removed by a signal peptidase during or immediately following membrane transfer.

As used herein, a "protein of interest" or "polypeptide of interest" refers to the protein to be expressed and secreted by the host cell. The protein of interest may be any protein which up until now has been considered for expression in prokaryotes. The protein of interest may be either homologous or heterologous to the host. In the first case overexpression should be read as expression above normal levels in said host. In the latter case basically any expression is of course overexpression.

The terms "isolated" or "purified" as used herein refer to a nucleic acid or amino acid that is removed from at least one component with which it is naturally associated.

As used herein, the term "heterologous protein" refers to a protein or polypeptide that does not naturally occur in a host cell. Examples of heterologous proteins include enzymes such as hydrolases including proteases, cellulases, amylases, other carbohydrases, and lipases; isomerases such as racemases, epimerases, tautomerases, or mutases; transferases, kinases and phophatases. The heterologous gene may encode therapeutically significant proteins or peptides, such as growth factors, cytokines, ligands, receptors and inhibitors, as well as vaccines and antibodies. The gene may encode commercially important industrial proteins or peptides, such as proteases, carbohydrases such as amylases and glucoamylases, cellulases, oxidases and lipases. The gene of interest may be a naturally occurring gene, a mutated gene or a synthetic gene.

The term "homologous protein" refers to a protein or polypeptide native or naturally occurring in a host cell. The invention includes host cells producing the homologous protein via recombinant DNA technology. The present invention encompasses a host cell having a deletion or interruption of the nucleic acid encoding the naturally occurring homologous protein, such as a protease, and having nucleic acid encoding the homologous protein re-introduced in a recombinant form. In another embodiment, the host cell produces the homologous protein.

The term "nucleic acid molecule" includes RNA, DNA and cDNA molecules. It will be understood that, as a result of the degeneracy of the genetic code, a multitude of nucleotide sequences encoding a given protein such as TatC and/or TatA may be produced. The present invention contemplates every possible variant nucleotide sequence, encoding TatC and/or TatA, all of which are possible given the degeneracy of the genetic code.

A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native cell.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in mammalian cells and where expression of the selectable marker confers to cells containing the expressed gene the ability to grow in the presence of a corresponding selective agent.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

"Chimeric gene" or "heterologous nucleic acid construct", as defined herein refers to a non-native gene (i.e., one that has been introduced into a host) that may be composed of parts of different genes, including regulatory elements. A chimeric gene construct for transformation of a host cell is typically composed of a transcriptional regulatory region (promoter) operably linked to a heterologous protein coding sequence, or, in a selectable marker chimeric gene, to a selectable marker gene encoding a protein conferring antibiotic resistance to transformed cells. A typical chimeric gene of the present invention, for transformation into a host cell, includes a transcriptional regulatory region that is constitutive or inducible, a signal peptide coding sequence, a protein coding sequence, and a terminator sequence. A chimeric gene construct may also include a second DNA sequence encoding a signal peptide if secretion of the target protein is desired.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm−5° C. (5° below the Tm of the probe); "high stringency" at about 5-10° below the Tm; "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5× Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the terms "transformed", "stably transformed" or "transgenic" with reference to a cell means the cell has a non-native (heterologous) nucleic acid sequence integrated into its genome or as an episomal plasmid that is maintained through two or more generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

The present invention provides novel gram-positive microorganism secretion factors and methods that can be used in microorganisms to ameliorate the bottleneck to protein secretion and the production of proteins in secreted form, in particular when the proteins are recombinantly introduced and overexpressed by the host cell. The present invention provides the secretion factors TatC and TatA derived from *Bacillus subtilis*. In particular, the TatCd and TatCy peptide, as well as the genes encoding them, are described herein.

The recent discovery of a ubiquitous translocation pathway, specifically required for proteins with a twin-arginine motif in their signal peptide, has focused interest on its membrane-bound components, one of which is known as TatC. Unlike most organisms of which the genome has been sequenced completely, the Gram-positive eubacterium *Bacillus subtilis* contains two tatC like genes, denoted tatCd and tatCy. The corresponding TatCd and TatCy proteins have the potential to be involved in the translocation of 27 proteins with putative twin-arginine signal peptides of which about 6 to 14 are likely to be secreted into the growth medium. Using a proteomic approach, we show that PhoD of *B. subtilis*, a phosphodiesterase belonging to a novel protein family of which all known members are synthesized with typical twin-arginine signal peptides, is secreted via the twin-arginine translocation pathway. Strikingly, TatCd is of major importance for the secretion of PhoD, whereas TatCy is not required for this process. Thus, TatC appears to be a specificity determinant for protein secretion via the Tat pathway. Based on our observations, we hypothesize that the TatC-determined pathway specificity is based on specific interactions between TatC-like proteins and other pathway components, such as TatA, of which three paralogues are present in *B. subtilis*.

Tat Nucleic Acid and Amino Acid Sequences

The TatCd polynucleotide having the sequence corresponding to the amino acid sequence as shown in FIG. 1 or 14 encodes the *Bacillus subtilis* secretion factor TatCd. The *Bacillus subtilis* TatCd was identified via a FASTA search of *Bacillus subtilis* translated genomic sequences using a consensus sequence of TatC derived from *E. coli*. A FASTA search of *Bacillus subtilis* translated genomic sequences with the *E. coli* TatC sequence alone did not identify the *B. subtilis* TatCd. The present invention provides gram-positive tatCd polynucleotides which may be used alone or together with other secretion factors in a gram-positive host cell for the purpose of increasing the secretion of desired heterologous or homologous proteins or polypeptides.

The present invention encompasses tatCd polynucleotide homologs encoding novel gram-positive microorganism tatC whether encoded by one or multiple polynucleotides which have at least 80%, or at least 90% or at least 95% identity to *B. subtilis* TatCd as long as the homolog encodes a protein that is able to function by modulating secretion in a gram-positive microorganism. As will be understood by the skilled artisan, due to the degeneracy of the genetic code, a variety of polynucleotides, i.e., tatC polynucleotide variants, can encode the *Bacillus subtilis* secretion factors TatCd. The present invention encompasses all such polynucleotides.

The present invention encompasses novel tatCd polynucleotide homologs encoding gram-positive microorganism TatC which has at least 80%, or at least 90% or at least 95% identity to *B. subtilis* as long as the homolog encodes a protein that has activity in a secretion.

Gram-positive polynucleotide homologs of *B. subtilis* tatCd may be obtained by standard procedures known in the art from, for example, cloned DNA (e.g., a DNA "library"), genomic DNA libraries, by chemical synthesis once identified, by cDNA cloning, or by the cloning of genomic DNA, or fragments thereof, purified from a desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) A preferred source is from genomic DNA. Nucleic acid sequences derived from genomic DNA may contain regulatory regions in addition to coding regions. Whatever the source, the isolated TatCd gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the tatCd may be accomplished in a number of ways. For example, a *B. subtilis* tatCd gene of the present invention or its specific RNA, or a fragment thereof, such as a probe or primer, may be isolated and labeled and then used in hybridization assays to detect a gram-positive tatC gene. (Benton, W. and Davis, R., 1977, *Science* 196:180; Grunstein, M. And Hogness, D., 1975, *Proc. Natl. Acad. Sci. USA* 72:3961). Those DNA fragments sharing substantial sequence similarity to the probe will hybridize under stringent conditions.

Accordingly, the present invention provides a method for the detection of gram-positive TatCd polynucleotide homologs which comprises hybridizing part or all of a nucleic acid sequence of *B. subtilis* tatCd with gram-positive microorganism nucleic acid of either genomic or cDNA origin.

Also included within the scope of the present invention are gram-positive microorganism polynucleotide sequences that are capable of hybridizing to the nucleotide sequence of *B. subtilis* tatCd under conditions of intermediate to maximal stringency. Hybridization conditions are based on the melting temperature (Tm) of the nucleic acid binding complex, as taught in Berger and Kimmel (1987, *Guide to Molecular Cloning Techniques, Methods in Enzymology*. Vol 152, Academic Press, San Diego Calif.) incorporated herein by reference, and confer a defined "stringency" as explained below.

Also included within the scope of the present invention are novel gram-positive microorganism tatC polynucleotide sequences that are capable of hybridizing to part or all of the tatC nucleotide sequence of Figure ? under conditions of intermediate to maximal stringency. Hybridization conditions are based on the melting temperature (Tm) of the nucleic acid binding complex, as taught in Berger and Kimmel (1987, *Guide to Molecular Cloning Techniques*, Methods in Enzymology, Vol 152, Academic Press, San Diego Calif.) incorporated herein by reference, and confer a defined "stringency" as explained below.

"Maximum stringency" typically occurs at about Tm–5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

The term "hybridization" as used herein shall include "the process by which a strand of nucleic acid joins with a complementary strand through base pairing" (Coombs J (1994) *Dictionary of Biotechnology*, Stockton Press, New York N.Y.).

The process of amplification as carried out in polymerase chain reaction (PCR) technologies is described in Dieffenbach C W and G S Dveksler (1995, *PCR Primer, a Laboratory Manual*, Cold Spring Harbor Press, Plainview N.Y.). A nucleic acid sequence of at least about 10 nucleotides and as many as about 60 nucleotides from the TatCd nucleotide sequence of Figure ?, preferably about 12 to 30 nucleotides, and more preferably about 20-25 nucleotides can be used as a probe or PCR primer.

The *B. subtilis* tatCd polynucleotide corresponding to the amino acid sequence as shown in FIG. 1 or 14 encodes *B. subtilis* TatCd. The present invention encompasses novel gram positive microorganism amino acid variants of the amino acid sequence shown in FIG. 1 or 14 that are at least 80% identical, at least 90% identical and at least 95% identical to the sequence shown in FIG. 1 or 14 as long as the amino acid sequence variant is able to function by modulating secretion of proteins in gram-positive microorganisms.

The secretion factor TatCd as shown in FIG. 1 was subjected to a FASTA (Lipmann Pearson routine) amino acid search against a consensus amino acid sequence for TatCd. The amino acid alignment is shown in FIG. 1.

Expression Systems

The present invention provides expression systems for the enhanced production and secretion of desired heterologous or homologous proteins in a host microorganism.

I. Coding Sequences

In the present invention, the vector comprises at least one copy of nucleic acid encoding a gram-positive microorganism TatC and/or TatA secretion factor and preferably comprises multiple copies. In a preferred embodiment, the gram-positive microorganism is *Bacillus*. In another preferred embodiment, the gram-positive microorganism is *Bacillus subtilis*. In a preferred embodiment, polynucleotides which encode *B. subtilis* TatC and/or TatA, or fragments thereof, or fusion proteins or polynucleotide homolog sequences that encode amino acid variants of TatC and/or TatA, may be used to generate recombinant DNA molecules that direct the expression of TatC and/or TatA, or amino acid variants thereof, respectively, in gram-positive host cells. In a preferred embodiment, the host cell belongs to the genus *Bacillus*. In another preferred embodiment, the host cell is *B. subtilis*.

As will be understood by those of skill in the art, it may be advantageous to produce polynucleotide sequences possessing non-naturally occurring codons. Codons preferred by a particular gram-positive host cell (Murray E et al (1989) Nuc Acids Res 17:477-508) can be selected, for example, to increase the rate of expression or to produce recombinant RNA transcripts having desirable properties, such as a longer half-life, than transcripts produced from naturally occurring sequence.

Altered gram positive tatC and/or tatA polynucleotide sequences which may be used in accordance with the invention include deletions, insertions or substitutions of different nucleotide residues resulting in a polynucleotide that encodes the same or a functionally equivalent TatC and/or TatA homolog, respectively. As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring gram positive TatC and/or TatA.

As used herein "substitution" results from the replacement of one or more nucleotides or amino acids by different nucleotides or amino acids, respectively.

The encoded protein may also show deletions, insertions or substitutions of amino acid residues which produce a silent change and result in a functionally equivalent gram-positive TatC and/or TatA variant. Deliberate amino acid substitutions may be made on the basis of similarity in polarity, charge, solubility, hydrophobicity, hydrophilicity, and/or the amphipathic nature of the residues as long as the variant retains the ability to modulate secretion. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylalanine, and tyrosine.

The TatC and/or TatA polynucleotides of the present invention may be engineered in order to modify the cloning, processing and/or expression of the gene product. For example, mutations may be introduced using techniques which are well known in the art, e.g., site-directed mutagenesis to insert new restriction sites, to alter glycosylation patterns or to change codon preference, for example.

In one embodiment of the present invention, a TatC and/or TatA polynucleotide may be ligated to a heterologous sequence to encode a fusion protein. A fusion protein may also be engineered to contain a cleavage site located between the TatC and/or TatA nucleotide sequence and the heterologous protein sequence, so that the TatC and/or TatA protein may be cleaved and purified away from the heterologous moiety.

II. Vector Sequences

Expression vectors used in expressing the secretion factors of the present invention in gram-positive microorganisms comprise at least one promoter associated with a gram-positive tatC and/or tatA, which promoter is functional in the host cell. In one embodiment of the present invention, the promoter is the wild-type promoter for the selected secretion factor and in another embodiment of the present invention, the promoter is heterologous to the secretion factor, but still functional in the host cell.

Additional promoters associated with heterologous nucleic acid encoding desired proteins or polypeptides may be introduced via recombinant DNA techniques. In one embodiment of the present invention, the host cell is capable of overexpressing a heterologous protein or polypeptide and nucleic acid encoding one or more secretion factor(s) is(are) recombinantly introduced. In one preferred embodiment of the present invention, nucleic acid encoding TatC and/or TatA is stably integrated into the microorganism genome. In another embodiment, the host cell is engineered to overexpress a secretion factor of the present invention and nucleic acid encoding the heterologous protein or polypeptide is introduced via recombinant DNA techniques. The present invention encompasses gram-positive host cells that are capable of overexpressing other secretion factors known to those of skill in the art, or other secretion factors known to those of skill in the art or identified in the future.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term selectable marker refers to a gene capable of expression in the gram-positive host which allows for ease of selection of those hosts containing the vector. Examples of such selectable markers include but are not limited to antibiotics, such as, erythromycin, actinomycin, chloramphenicol and tetracycline.

III. Transformation

In one embodiment of the present invention, nucleic acid encoding one or more gram-positive secretion factor(s) of the present invention is introduced into a gram-positive host cell via an expression vector capable of replicating within the host cell. Suitable replicating plasmids for *Bacillus* are described in Molecular Biological Methods for *Bacillus*, Ed. Harwood and Cutting, John Wiley & Sons, 1990, hereby expressly incorporated by reference; see chapter 3 on plasmids. Suitable replicating plasmids for *B. subtilis* are listed on page 92.

In another embodiment, nucleic acid encoding a gram-positive microorganism tatC and/or tatA stably integrated into the microorganism genome. Preferred gram-positive host cells are from the genus *Bacillus*. Another preferred gram-positive host cell is *B. subtilis*. Several strategies have been described in the literature for the direct cloning of DNA in *Bacillus*. Plasmid marker rescue transformation involves the uptake of a donor plasmid by competent cells carrying a partially homologous resident plasmid (Contente et al., *Plasmid* 2:555-571 (1979); Haima et al., *Mol. Gen. Genet.* 223: 185-191 (1990); Weinrauch et al., *J. Bacteriol.* 154(3):1077-1087 (1983); and Weinrauch et al., *J. Bacteriol.* 169(3):1205-1211 (1987)). The incoming donor plasmid recombines with the homologous region of the resident "helper" plasmid in a process that mimics chromosomal transformation.

Transformation by protoplast transformation is described for *B. subtilis* in Chang and Cohen, (1979) *Mol. Gen. Genet.* 168:111-115; for *B. megaterium* in Vorobjeva et al., (1980) FEMS Microbiol. Letters 7:261-263; for *B. amyloliquefaciens* in Smith et al., (1986) Appl. and Env. Microbiol. 51:634; for *B. thuringiensis* in Fisher et al., (1981) Arch. Microbiol. 139:213-217; for *B. sphaericus* in McDonald (1984) J. Gen. Microbiol. 130:203; and *B. larvae* in Bakhiet et al., (1985) 49:577. Mann et al., (1986, Current Microbiol. 13:131-135) report on transformation of *Bacillus* protoplasts and Holubova, (1985) Folia Microbiol. 30:97) disclose methods for introducing DNA into protoplasts using DNA containing liposomes.

Identification of Transformants

Although the presence/absence of marker gene expression suggests that the gene of interest is also present, its presence and expression should be confirmed. For example, if the nucleic acid encoding tatC and/or tatA is inserted within a marker gene sequence, recombinant cells containing the insert can be identified by the absence of marker gene function. Alternatively, a marker gene can be placed in tandem with nucleic acid encoding the secretion factor under the control of a single promoter. Expression of the marker gene in response to induction or selection usually indicates expression of the secretion factor as well.

Alternatively, host cells which contain the coding sequence for a secretion factor and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the tatC and/or tatA polynucleotide sequence can be detected by DNA-DNA or DNA-RNA hybridization or amplification using probes, portions or fragments derived from the *B. subtilis* tatC and/or tatA polynucleotide.

Secretion Assays

Means for determining the levels of secretion of a heterologous or homologous protein in a gram-positive host cell and detecting secreted proteins include, using either polyclonal or monoclonal antibodies specific for the protein. Examples include enzyme-linked immunosorbent assay (ELISA), radioimmunoassay (RIA) and fluorescent activated cell sorting (FACS). These and other assays are described, among other places, in Hampton R et al (1990, *Serological*

Methods, a Laboratory Manual, APS Press, St Paul Minn.) and Maddox D E et al (1983, J Exp Med 158:1211).

A wide variety of labels and conjugation techniques are known by those skilled in the art and can be used in various nucleic and amino acid assays. Means for producing labeled hybridization or PCR probes for detecting specific polynucleotide sequences include oligolabeling, nick translation, end-labeling or PCR amplification using a labeled nucleotide. Alternatively, the nucleotide sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 and incorporated herein by reference.

Purification of Proteins

Host cells transformed with polynucleotide sequences encoding heterologous or homologous protein may be cultured under conditions suitable for the expression and recovery of the encoded protein from cell culture. The protein produced by a recombinant host cell comprising a secretion factor of the present invention will be secreted into the culture media. Other recombinant constructions may join the heterologous or homologous polynucleotide sequences to nucleotide sequence encoding a polypeptide domain which will facilitate purification of soluble proteins (Kroll D J et al (1993) DNA Cell Biol 12:441-53).

Such purification facilitating domains include, but are not limited to, metal chelating peptides such as histidine-tryptophan modules that allow purification on immobilized metals (Porath J (1992) Protein Expr Purif 3:263-281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein can be used to facilitate purification.

In the present studies, we demonstrate for the first time that a functional Tat pathway, required for secretion of the PhoD protein, exists in the Gram-positive eubacterium B. subtilis. The TatCd protein, specified by one of the two tatC genes of B. subtilis, plays a critical role in this secretion pathway. In contrast, the TatCy protein appears to be of minor importance for PhoD secretion. Even though no particular function for TatCy was identified, our results show that the corresponding gene is transcribed under conditions of phosphate starvation when TatCd fulfils its critical role in PhoD secretion. Furthermore, as inferred from the fact that low levels of PhoD secretion by B. subtilis ΔtatCd (but never by tatCd-tatCy double mutants) were observed in some experiments, TatCy seems to be actively involved in RR-pre-protein translocation. Notably, these observations imply that TatC is a specificity determinant for protein secretion via the Tat pathway. In fact, our observation that the secretion of PhoD was increased in the absence of TatCy suggests that abortive interactions between pre-PhoD and TatCy or TatCy-containing translocases can occur. Nevertheless, alternative, more indirect explanations for this observation can presently not be excluded. Interestingly, the positive effect of the tatCy mutation on PhoD secretion is reminiscent of the effect that was observed when certain genes (i.e. sipS and/or sipU) for paralogous type I signal peptidases of B. subtilis were disrupted. This resulted in significantly improved rates of processing of the α-amylase AmyQ precursor by the remaining type I signal peptidases (i.e. SipT, SipV and/or SipW; Tjalsma et al. (1998) Genes Dev. 12, 2318-2331, Tjalsma et al. (1997) J. Biol. Chem. 272, 25983-25992, and Bolhuis et al. (1996). Mol. Microbiol. 22, 605-618). Taken together, these observations suggest that, in general, the presence of two or more paralogous secretion machinery components in B. subtilis may result in, as yet undefined, abortive interactions with certain secretory pre-proteins.

The PhoD protein of B. subtilis is synthesized with a typical RR-signal peptide that contains a long hydrophilic N-region with a consensus RR-motif, and a mildly hydrophobic H-region (Table I). In fact, the RR-signal peptide of PhoD contains no detectably atypical features for RR-signal peptides (see: Berks, B. C. (1996) Mol. Microbiol. 22, 393-404) and, therefore, it is presently not clear why PhoD specifically requires the presence of TatCd for efficient secretion. Strikingly, the secretion of YdhF, the only other protein with a predicted RR-signal peptide that could, so far, be identified through 2D-gel electrophoresis, was not affected in the ΔtatCd-ΔtatCy mutant. This observation shows that the RR-motif in the YdhF signal peptide does not direct this protein into the Tat pathway. Instead, YdhF is, most likely, secreted via the Sec pathway, which could be due to the relatively short, but highly hydrophobic, H-region of the YdhF signal peptide. Similarly, the WapA and WprA proteins of B. subtilis, which have predicted RR-signal peptides (Table I), were recently shown to be secreted in a strongly Ffh- and SecA-dependent manner (Hirose et al. (2000) Microbiology 146, 65-75), which implies that these proteins do not use the Tat pathway. Even though the H-regions of these signal peptides are of similar size as that of the PhoD signal peptide, they are significantly more hydrophobic. The latter observation suggests that, like in E. coli (Cristóbal et al. (1999) EMBO J. 18, 2982-2990), the hydrophobicity of the H-region is an important determinant that allows the cell to discriminate between Sec-type and RR-signal peptides. Notably, the predicted RR-motifs of WapA, WprA and YdhF are also different from previously described RR-signal peptides, because they contain Lys or Ser residues at the +3 position relative to the twin-arginines (Table I). In fact, hydrophilic residues are completely absent from the +2 and +3 positions, relative to the twin-arginines of known RR-signal peptides. (Berks, B. C. (1996) Mol. Microbiol. 22, 393-404, Brink et al. (1998) FEBS Lett. 434, 425-430, Sargent et al. (1998) EMBO J. 17, 3640-3650, Chaddock et al. (1995) EMBO J. 14, 2715-2722, Sargent et al. (1999) J. Biol. Chem. 274, 36073-36082, and Santini et al., (1998) EMBO J. 17, 101-112). If low overall hydrophobicity and the presence of hydrophobic residues at the +2 and +3 positions are used as criteria for the prediction of RR-signal peptides, the total number of predicted B. subtilis signal peptides of this type can be reduced from 27 to 11. Notably, of these 11 pre-proteins, 4 contain additional transmembrane segments, and 1 lacks a signal peptidase cleavage site. Thus, based on these more stringent criteria, one would predict that merely 6 proteins of B. subtilis (i.e. AlbB, LipA, PhoD, YkpC, YkuE, and YwbN) are secreted into the growth medium via the Tat pathway. This would explain why the secretion of only one protein, PhoD, was detectably affected in *B. subtilis* ΔtatCd-ΔtatCy under conditions of phosphate starvation. In this respect, it is important to note that TatC-dependent secretion of some other proteins with (predicted) RR-signal peptides may have remained unnoticed in the present studies, because they are expressed at very low levels under conditions of phosphate starvation. Furthermore, it is conceivable that other TatC-dependent proteins were missed in the 2D-gel electrophoretic analysis, due to their poor separation in the first dimension.

Interestingly, the YdhF protein was also predicted to be a lipoprotein (Table I; Tjalsma et al. (1999) *J. Biol. Chem.* 274, 1698-1707). The fact that YdhF was found in the growth medium either suggests that this prediction was wrong, or that YdhF is released into the growth medium via a secondary processing event that follows cleavage by the lipoprotein-specific (type II) signal peptidase (Prágai et al. (1997) *Microbiology* 143, 1327-1333). Such secondary processing events have been described previously for other *Bacillus* lipoproteins (see: Tjalsma et al. (1999) *J. Biol. Chem.* 274, 1698-1707). In fact, the latter possibility most likely explains why the phosphate-binding protein PstS, which is a typical lipoprotein (previously known as YqgG; Tjalsma et al. (1999) *J. Biol. Chem.* 274, 1698-1707, and Qi, Y., and Hulett, F. M. (1998) *J. Bacteriol.* 180, 4007-4010), was found in the growth medium. As expected for lipoproteins, significant amounts of PstS were also present in a cell-associated form (Antelmann, H., Scharf, C., and Hecker, M., (2000) *J. Bacteriol.* in press, and Eymann et al. (1996) *Microbiology* 142, 3163-3170).

One of the outstanding features of the Tat pathway of *E. coli* is its ability to translocate fully-folded proteins that bind cofactors prior to export from the cytoplasm, and even multimeric enzyme complexes (Berks, B. C. (1996) *Mol. Microbiol.* 22, 393-404, Weiner et al. (1998) *Cell* 93, 93-101, Santini et al. (1998) *EMBO J.* 17, 101-112, and Rodrigue et al. (1999) *J. Biol. Chem.* 274, 13223-13228). Similarly, the thylakoidal Tat pathway has been shown to translocate folded proteins (Bogsch et al. (1997) *EMBO J.* 16, 3851-3859, and Hynds et al. (1998) *J. Biol. Chem.* 273, 34868-34874). Thus, it seems as if this pathway is used for the transport of proteins that are Sec-incompatible, either because they must fold before translocation, or because they fold too rapidly or tightly to allow transport via the Sec-system, which is known to transport proteins in an unfolded conformation (see: Dalbey, R. E., and Robinson, C. (1999) *Trends Biochem. Sci.* 24, 17-22). Consistent with this idea, folded pre-proteins, some of which were biologically active, were shown to accumulate in tat mutants of *E. coli* (Sargent et al. (1998) *EMBO J.* 17, 3640-3650, Bogsch et al. (1998) *J. Biol. Chem.* 273, 18003-18006, Weiner et al. (1998) *Cell* 93, 93-101, and Sargent et al. (1999) *J. Biol. Chem.* 274, 36073-36082). Therefore, it is conceivable that the Tat pathway of *B. subtilis* is also involved in the transport of folded cofactor-binding proteins. This view is supported by the observation that the iron-sulfur cluster-binding Rieske protein QcrA of *B. subtilis* (Yu et al. (1995) *J. Bacteriol.* 177, 6751-6760) is synthesised with a predicted RR-signal peptide (Table I). Nevertheless, compared to the parental strain, pre-PhoD accumulation was not increased in *B. subtilis* ΔtatCd-ΔtatCy. This suggests that pre-PhoD is either not folded prior to translocation, or that folded pre-PhoD is sensitive to cytosolic proteases of *B. subtilis*. We favor the first possibility, because most native *B. subtilis* proteins are highly resistant to proteolysis, provided that they are properly folded (see: Stephenson et al. (1998) *Appl. Environ. Microbiol.* 64, 2875-2881, Bolhuis et al. (1999) *J. Biol. Chem.* 274, 15865-15868, and Bolhuis et al. (1999) *Appl. Environ. Microbiol.* 65, 2934-2941). Consistent with the idea that pre-PhoD could be secreted in a loosely folded or unfolded conformation is the observation that loosely folded proteins can be transported via the thylakoidal Tat pathway (Bogsch et al. (1997) *EMBO J.* 16, 3851-3859, and Hynds et al. (1998) *J. Biol. Chem.* 273, 34868-34874). Strikingly, the four known homologues of PhoD, all of which were identified in *Streptomyces* species, are synthesised with a typical RR-signal peptide (Table IV). Thus it seems that PhoD-like proteins belong to a novel family of proteins with an as yet undefined requirement for translocation via the Tat pathway. In this respect, it is interesting to note that the N-regions of the RR-signal peptides of PhoD and PhoD-like proteins are among the longest N-regions of known RR-signal peptides (see: Berks, B. C. (1996) *Mol. Microbiol.* 22, 393-404).

Finally, one of the most striking results of our present studies is the observation that TatC is a specificity determinant for protein secretion via the Tat pathway of *B. subtilis*. Interestingly, this finding questions to some extent the hypothesis that the TatA-like components of this pathway have a receptor-like function (Chanal et al. (1998) *Mol. Microbiol.* 30, 674-676, and Settles et al. (1997) *Science* 278, 1467-1470). Instead, it suggests that TatC-like proteins recognise specific elements of certain exported proteins, such as the RR-signal peptide. Thus, our results might represent the first experimental support for the 'sea anemone' model of Berks et. al. (*Mol. Microbiol.* (2000) 5, 260-274) in which, on the basis of theoretical considerations, it is proposed that the TatABE proteins form a protein-conducting channel, while the TatC protein acts as an RR-signal peptide receptor. Alternatively, it is still conceivable that certain proteins with RR-signal peptides are recognized by TatA-like proteins, provided that a specific TatC-like partner protein is present. A third possibility would be that specific TatA- and TatC-like partner proteins are jointly involved in substrate recognition. The fact that neither TatAc nor TatAd of *B. subtilis* were able to complement tatA, tatB or tatE mutations in *E. coli*, and that TatCd of *B. subtilis* was unable to complement the *E. coli* tatC mutation (our unpublished observations), suggests that the TatC-determined pathway specificity, as described in the present studies, is based on specific interactions between TatA- and TatC-like proteins. If so, this implies that *B. subtilis* contains two parallel routes for twin-arginine translocation, one of which involves the TatCd protein. As shown in the present studies, the TatCd-dependent translocation appears to be activated specifically under conditions of phosphate starvation, perhaps with the sole purpose of translocating PhoD. Similar to the situation in *B. subtilis*, parallel routes for twin-arginine translocation may be present in other organisms, such as *Archaeoglobus fulgidus*, which was shown to contain two paralogous tatC-like genes (Berks et al. (2000) *Mol. Microbiol.* 5, 260-274, and Klenk et al. (1997) *Nature* 390, 364-370).

Additional work carried out in support of the present invention indicates that both tatCd and tatCy may be TAT components and responsible for secretion of other genes as well. In fact, with reference to FIG. 6, a tatCd deletion totally abolishes the secretion of LipA. FIG. 6 however suggests also that, while TatCd is the primary TAT component, TatCy plays some role on the secretion of LipA (although not as stringent as TatCd).

The bacterial twin-arginine translocation (Tat) pathway has been recently described for PhoD of *Bacillus subtilis*, a phosphodiesterase containing a twin-arginine signal peptide. The expression of phoD, induced in response to phosphate depletion, is co-regulated with expression of tatAd and tatCd genes localized downstream of phoD. While tatCd was of major importance for the secretion of PhoD, the second copy of a tatC (tatCy) was not required for this process. To characterise specificity of PhoD transport further, translocation of PhoD was investigated in *E. coli*. Using gene fusions, we analysed the particular role of the signal peptide and the mature region of PhoD in canalising the transport route. A hybrid protein consisting of the signal peptide of TEM-β-lactainase and mature PhoD was transported Sec-dependent indicating that the mature part of PhoD does not contain information canalising the selected translocation route. Pre-PhoD as well as a fusion protein consisting of the signal peptide of PhoD ($SP_{phoD}$) and β-galactosidase (LacZ) remained cytosolic in the *Escherichia coli*. Thus, $SP_{phoD}$ appears to be not recognised by *E. coli* transport systems. Co-expression of *B. subtilis* $tat_d/C_d$ genes resulted in the processing of $SP_{phoD}$-LacZ and periplasmic localisation of LacZ illustrating a close substrate-Tat component specificity of the PhoD-Tat$A_d/C_d$ transport system. While blockage of the Sec-dependent transport did not affect the localisation of $SP_{phoD}$-LacZ, translocation and processing was dependent on the pH gradient of the cytosolic membrane. TatAd/Cd-mediated transport of $SP_{phoD}$-LacZ was observed in absence of the *E. coli* Tat proteins indicating $SP_{phoD}$-peptides and its adopted TatAd/Cd protein pair form an autonomous Tat system in *E. coli*. Thus, the minimal requirement of an active Tat-dependent protein translocation system consists of a twin-arginine signal peptide containing Tat substrate, its specific TatA/C proteins and the pH-gradient across the cytosolic membrane.

The following preparations and examples are given to enable those skilled in the art to more clearly understand and practice the present invention. They should not be considered as limiting the scope and/or spirit of the invention, but merely as being illustrative and representative thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds); TLC (thin layer achromatography); TY, trypton/yeast extract; Ap, ampicillin; DTT, dithiotreitol; Em, erythromycin; HPDM, high phosphate defined medium; IPG, immobilized pH gradient; IPTG, isopropyl-β-D-thiogalactopyranoside; Km, kanamycin; LPDM, low phosphate defined medium; MM, minimal medium; OD, optical density; PAGE, polyacrylamide gel electrophoresis; PCR, polymerase chain reaction; Sp, spectinomycin; SSM, Schaeffer's sporulation medium; 2D, two-dimensional.

EXAMPLE 1

Identification of tat Genes of *B. subtilis*

In order to investigate whether *B. subtilis* contains a potential Tat pathway, a search for homologues of *E. coli* Tat proteins was performed, using the complete sequence of the *B. subtilis* genome (Kunst et al. (1997) Nature 390, 249-256). First, sequence comparisons revealed that *B. subtilis* contains three paralogous genes (i.e., yczB, ydiI and ynzA) that specify proteins with sequence similarity to the three paralogous *E. coli* TatA, TatB and TatE proteins. Specifically, the YdiI protein (57 residues), which was renamed TatAy, showed the highest degree of sequence similarity with the *E. coli* TatA protein (58% identical residues and conservative replacements); the YczB protein (70 residues), which was renamed TatAd, showed the highest degree of sequence similarity with the *E. coli* TatB protein (54% identical residues and conservative replacements); and the YnzA protein (62 residues), which was renamed TatAc, showed the highest degree of sequence similarity with the *E. coli* TatB protein (53% identical residues and conservative replacements). All three *B. subtilis* proteins were renamed TatA to avoid possible mis-interpretations with respect to their respective functions, which are presently unknown. Like TatA, TatB, and TatE of *E. coli*, the three TatA proteins of *B. subtilis* appear to have one amino-terminal membrane spanning domain (FIG. 1A), and the carboxyl-terminal parts of these proteins are predicted to face the cytoplasm. Even though TatAc, TatAd and TatAy of *B. subtilis* show significant similarity to TatA, TatB and TatE of *E. coli* when the amino acid sequences of these proteins are compared pairwise, only a limited number of residues is conserved in all six amino acid sequences (17% identical residues and conservative replacements; FIG. 1A).

Second, in contrast to *E. coli*, which contains a unique tatC gene (10), *B. subtilis* was shown to contain two paralogous tatC-like genes (ie. ycbT and ydiJ). The YcbT protein (245 residues), which was renamed TatCd, and the YdiJ protein (254 residues), which was renamed TatCy, showed significant similarity to the *E. coli* TatC protein (57% identical residues and conservative replacements in the three aligned sequences; FIG. 1B). Like TatC of *E. coli*, TatCd and TatCy of *B. subtilis* have six potential transmembrane segments (FIG. 1B), and the amino-termini of these proteins are predicted to face the cytoplasm (data not shown).

In contrast to *E. coli*, in which the tatA, tatB and tatC genes form one operon while the tatE gene is monocistronic (Sargent et al. (1998) *EMBO J.* 17, 3640-3650), the tat genes of *B. subtilis* are located at three distinct chromosomal regions. Two of these regions contain adjacent tatA and tatC genes, the tatAd and tatAy genes being located immediately upstream of the tatCd and tatCy genes, respectively (FIG. 2). Strikingly, the tatAd and tatCd genes, which map at 24.4 o on the *B. subtilis* chromosome, are located immediately downstream of the phoD gene, specifying a secreted protein with a putative RR-signal peptide (Table I). Furthermore, the tatAy and tatCy genes are located at 55.30° on the *B. subtilis* chromosome, within a cluster of genes with unknown function (FIG. 2), and the tatAc gene is located at 162.7° on the *B. subtilis* chromosome (data not shown), immediately downstream of the cotC gene specifying a spore coat protein (Donovan et al. (1987) *J. Mol. Biol.* 196, 1-10). Finally, a tatD-like gene, denoted yabD, is located at 4.1° on the *B. subtilis* chromosome, immediately downstream of the metS gene encoding a methionyl-tRNA synthetase (data not shown).

Taken together, these observations strongly suggest that *B. subtilis* has a Tat pathway for the translocation of proteins with RR-signal peptides across the cytoplasmic membrane. Furthermore, the observation that the tatAd and tatCd genes are located downstream of the phoD gene, which is a member of the pho regulon (Eder et al. (1996) *Microbiology* 142, 2041-2047), suggests that the tatAd and tatCd genes might be exclusively expressed under conditions of phosphate starvation.

EXAMPLE 2

TatC-dependent Secretion of the PhoD Protein

To investigate whether an active Tat pathway exists in *B. subtilis*, various single and double tatC mutants were constructed. To this purpose, the tatCd gene was either disrupted with a Km resistance marker, or it was placed under the control of the IPTG-dependent Pspac promoter of plasmid pMutin2, resulting in the B. subtilis strains ΔtatCd and ItatCd, respectively (FIGS. 3, A and B). Similarly, the tatCy gene was either disrupted with an Sp resistance marker, or it was placed under the control of the IPTG-dependent Pspac promoter of plasmid pMutin2, resulting in the B. subtilis strains ΔtatCy and ItatCy, respectively (FIGS. 3, A and C). Double tatC-tatCy mutants were constructed by transforming the ΔtatCy mutant with chromosomal DNA of the ΔtatCd or ItatCd mutant strains.

Table II lists the plasmids and bacterial strains used. TY[1] medium (tryptone/yeast extract) contained Bacto tryptone (1%), Bacto yeast extract (0.5%) and NaCl (1%). Minimal medium (MM) was prepared as described in Tjalsma et al. (1998) *Genes Dev.* 12, 2318-2331. Schaeffer's sporulation medium (SSM) was prepared as described in Schaeffer et al. (1965) *Proc. Natl. Acad. Sci. USA* 271, 5463-5467. High phosphate (HPDM) and low phosphate (LPDM) defined media were prepared as described in Müller et al. (1997) *Microbiology* 143, 947-956. To test anaeorobic growth, S7 medium was prepared as described in van Dijl et al. (1991) *J. Gen. Microbiol.* 137, 2073-2083 and van Dijl et al. (1991) *Mol. Gen. Genet.* 227, 40-48 and supplemented with $NaNO_3$ (0.2%) and glycerol (2%). When required, media for *E. coli* were supplemented with ampicillin (Ap; 100 μg/ml), erythromycin (Em; 100 μg/ml), kanamycin (Km; 40 μg/ml), or spectinomycin (Sp; 100 μg/ml); media for *B. subtilis* were supplemented with Em (1 μg/ml), Km (10 μg/ml), Sp (100 μg/ml), and/or isopropyl-β-D-thiogalactopyranoside (IPTG; 100 μM).

Procedures for DNA purification, restriction, ligation, agarose gel electrophoresis, and transformation of *E. coli* were carried out as described in Sambrook et al. (1989) *Molecular Cloning: A laboratory Manual*, 2nd Ed., Cold Spring Harbor Laboratory, Cold Spring Harbor, N.Y. Enzymes were from Roche Molecular Biochemicals. *B. subtilis* was transformed as described in Tjalsma et al. (1997) *J. Biol. Chem.* 272, 25983-25992. PCR (polymerase chain reaction) was carried out with the Pwo DNA polymerase (New England Biolabs) as described in van Dijl et al. (1995) *J. Biol. Chem.* 270, 3611-3618.

To construct *B. subtilis* ItatCd, the 5' region of the tatCd gene was amplified by PCR with the primers JJ14bT (5'-CCC AAG CTT ATG AAA GGG AGG GCT TTT TTG AAT GG-3') containing a HindIII site, and JJ15bT (5'-GCG GAT CCA AAG CTG AGC ACG ATC GG-3') containing a BamHI site. The amplified fragment was cleaved with HindIII and BamHI, and cloned in the corresponding sites of pMutin2 (Vagner et al. (1998) *Microbiol.* 144, 3097-3104), resulting in pMICd1. *B. subtilis* ItatCd was obtained by a Campbell-type integration (single cross-over) of pMICd1 into the tatCd region of the chromosome.

To construct *B. subtilis* ItatCy, the 5' region of the tatCy gene was amplified by PCR with the primers JJ03iJ (5'-CCC AAG CTT AAA AAG AAA GAA GAT CAG TAA GTT AGG ATG-3') containing a HindIII site, and JJ04iJ (5'-GCG GAT CCA AGT CCT GAG AAA TCC G-3') containing a BamHI site. The amplified fragment was cleaved with HindIII and BamHI, and cloned in the corresponding sites of pMutin2, resulting in pMICy1. *B. subtilis* ItatCy was obtained by a Campbell-type integration (single cross-over) of pMICy1 into the tatCy region of the chromosome.

To construct *B. subtilis* ΔtatCd, the tatCd gene was amplified by PCR with primer JJ33Cdd (5'-GGA ATT CGT GGG ACG GCT ACC-3') containing an EcoRI site and 5' sequences of tatCd, and primer JJ34Cdd (5'-CGG GAT CCA TCA TGG GAA GCG-3') containing a BamHI site and 3' sequences of tatCd. Next, the PCR-amplified fragment was cleaved with EcoRI and BamHI and ligated into the corresponding sites of pUC21, resulting in pJCd1. Plasmid pJCd2 was obtained by replacing an internal BclI-AccI fragment of the tatCd gene in pJCd1 with a pDG792-derived Km resistance marker, flanked by BamHI and ClaI restriction sites. Finally, *B. subtilis* ΔtatCd was obtained by a double cross-over recombination event between the disrupted tatCd gene of pJCd2 and the chromosomal tatCd gene.

To construct *B. subtilis* ΔtatCy, the tatCy gene was amplified by PCR with primer JJ29Cyd (5'-GGG GTA CCG GAA AAC GCT TGA TCA GG-3') containing a KpnI site and 5' sequences of tatCy, and primer JJ30Cyd (5'-CGG GAT CCT TTG GGC GAT AGC C-3') containing a BamHI site and 3' sequences of tatCy. Next, the PCR-amplified fragment was cleaved with KpnI and BamHI and ligated into the Asp718 and BamHI sites of pUC21, resulting in pJCy1. Plasmid pJCy2 was obtained by ligating a pDG1726-derived Sp resistance marker, flanked by PstI restriction sites, into the unique PstI site of the tatCy gene in pJCy1. Finally, *B. subtiis* ΔtatCy was obtained by a double cross-over recombination event between the disrupted tatCy gene of pJCy2 and the chromosomal tatCy gene.

Double tatCd-tatCy mutants were constructed by transforming the ΔtatCy mutant with chromosomal DNA of the ΔtatCd or ItatCd mutant strains. Correct integration of plasmids or resistance markers into the chromosome of *B. subtilis* was verified by Southern blotting. The BLAST algorithm (Altschul et al. (1997) *Nucleic Acids Res.* 25, 3389-3402) was used for protein comparisons in GenBank. Protein sequence alignments were carried out with the ClustalW program (Thompson et al. (1994) *Nucleic Acids Res.* 22, 4673-4680), using the Blosum matrices, or version 6.7 of the PCGene Analysis Program (Intelligenetics Inc.). Putative transmembrane segments, and their membrane topologies were predicted with the TopPred2 algorithm (Sipos et al. (1993) *Eur. J. Biochem.* 213, 1333-1340 and Cserzo et al. (1997) *Protein Eng.* 10, 673-676).

Competence and sporulation—Competence for DNA binding and uptake was determined by transformation with plasmid or chromosomal DNA (Bron et al. (1972) *Mutat. Res.* 15, 1-10). The efficiency of sporulation was determined by overnight growth in SSM medium, killing of cells with 0.1 volume chloroform, and subsequent plating.

Western blot analysis and immunodetection—To detect PhoB and PhoD, *B. subtilis* cells were separated from the growth medium by centrifugation (2 min, 14,000 rpm, room temperature). Proteins in the growth medium were concentrated 20-fold upon precipitation with trichloroacetic acid, and samples for SDS polyacrylamide gel electrophoresis (PAGE) were prepared as described previously in Laemmli, U. K. (1970) *Nature* 227, 680-685. After separation by SDS-PAGE, proteins were transferred to a nitrocellulose membrane (Schleicher and Schüll) as described in Towbin et al. (1979) *Proc. Natl. Acad. Sci. USA* 76, 4350-4354. PhoB and PhoD were visualized with specific antibodies (Müller, J. P., and Wagner, M. (1999) *FEMS Microbiol. Lett.* 180, 287-296) and alkaline phosphatase-conjugated goat anti-rabbit antibodies (SIGMA) according to the manufacturer's instructions.

Two-dimensional (2D) gel electrophoresis of secreted proteins. *B. subtilis* strains were grown at 37° C. under vigorous agitation in 1 liter of a synthetic medium (Antelmann et al. (1997) *J. Bacteriol.* 179, 7251-7256, and Antelmann et al., (2000) *J. Bacteriol.* in press) containing 0.16 mM $KH_2PO_4$ to induce a phosphate starvation response. After 1 hour of postexponential growth, cells were separated from the growth medium by centrifugation. The secreted proteins in the growth medium were precipitated overnight with ice-cold 10% trichloroacetic acid, and collected by centrifugation (40000 g, 2 h, 4° C.). The pellet was washed 3 times with 96% ethanol, dried and resuspended in 400 µl of rehydration solution containing 2 M thiourea, 8 M urea, 1% Nonidet P40, 20 mM DTT and 0.5% Pharmalyte (pH 3-10). Cells were disrupted by sonication as described in Eymann et al. (1996) *Microbiology* 142, 3163-3170, and cellular proteins were resuspended in rehydration solution as described above. Samples of secreted or cellular proteins in rehydration solution were used for the re-swelling of immobilized pH gradient (IPG) strips (pH range 3-10). Next, protein separation in the IPG strips (first dimension electrophoresis) was performed as recommended by the manufacturer (Amersham Pharmacia Biotech). Electrophoresis in the second dimension was performed as described in Bernhardt et al. (1997) *Microbiology* 143, 999-1017. The resulting 2D-gels were stained with silver nitrate (Blum et al. (1987) *Electrophoresis* 8, 93-99) or Coomassie Brilliant Blue R250.

Protein identification. In-gel tryptic digestion of proteins, separated by 2D gel electrophoresis, was performed using a peptide-collecting device (Otto et al. (1996) *Electrophoresis* 17, 1643-1650). To this purpose, 0.5 µl peptide solution was mixed with an equal volume of a saturated α-cyano-4-hydroxy cinnamic acid solution in 50% acetonitrile and 0.1% trifluoroacetic acid. The resulting mixture was applied to the sample template of a matrix-assisted laser desorption/ionization mass spectrometer (Voyager DE-STR, PerSeptive Biosystems). Peptide mass fingerprints were analysed using the 'MS-it'software, as provided by Baker and Clausner through http://prospector.ucsf.edu.

The fact that double tatCd-tatCy mutants could be obtained shows that TatC function is not essential for viability of *B. subtilis*, at least not when cells are grown aerobically in TY or minimal medium at 37° C., or anaerobically in S7 medium, supplemented with NaNO$_3$ (0.2%) and glycerol (2%) at 37° C. (data not shown). Furthermore, the ΔtatCd-ΔtatCy double mutation did not inhibit the development of competence for DNA binding and uptake, sporulation and the subsequent spore germination (data not shown), showing that these primitive developmental processes do not require TatC function.

The effects of single and double tatC mutations on protein secretion via the Tat pathway were studied using PhoD as a native reporter protein. To this purpose, tatC mutant strains were grown under conditions of phosphate starvation, using LPDM medium. As shown by Western blotting, the secretion of PhoD was strongly reduced in the ΔtatCd mutant strain and the ΔtatCd-ΔtatCy double mutant, whereas it was not affected or even improved in the ΔtatCy mutant strain (FIG. 4A). In contrast, the secretion of the alkaline phosphatase PhoB, which is dependent of the major (Sec) pathway for protein secretion (49), was not affected in the tatC mutants of *B. subtilis* (FIG. 4B). Notably, in some experiments, very low amounts of PhoD were detectable in the growth medium of *B. subtilis* ΔtatCd (data not shown), but never in that of ΔtatCd-ΔtatCy or ItatCd-ΔtatCy double mutants (FIGS. 4, A and C). As exemplified with the *B. subtilis* ItatCd-ΔtatCy double mutant strain, the cells of all tatC mutant strains contained similar amounts of pre-PhoD, which were comparable to those in the parental strain 168 (FIG. 4C; data not shown). Finally, 2D-gel electrophoresis of proteins in the medium of phosphate-starved cells of *B. subtilis* ΔtatCd-ΔtatCy or the parental strain 168 showed that PhoD is the only protein of which the secretion is detectably affected by the double tatC mutation under conditions of phosphate starvation (FIG. 5). As expected, the secretion of proteins lacking an RR-signal peptide, such as the glycerophosphoryl diester phosphodiesterase GlpQ, the pectate lyase Pel, the alkaline phosphatases PhoA and PhoB, the phosphate-binding protein PstS, the minor extracellular serine protease Vpr, the PBSX prophage protein XkdE and the protein with unknown function YncM, was not significantly affected by the double tatC mutation. Surprisingly, however, the secretion of the YdhF, a protein of unknown function, which does have a potential RR-signal peptide (Table I), was also not affected by the disruption of tatCd and tatCy (FIG. 5). Consistent with the above observations, no differences in the cellular proteomes of *B. subtilis* ΔtatCd-ΔtatCy and the parental strain 168 could be detected by 2D-gel electrophoresis (data not shown).

In summary, these results show that an active Tat pathway exists in *B. subtilis*, and that TatCd has a critical role in the secretion of PhoD.

EXAMPLE 3

Expression of tatCd and tatCy Genes

To study the expression of the tatCd and tatCy genes, the transcriptional tatCd-lacZ and tatCy-lacZ gene fusions, present in *B. subtilis* ItatCd and ItatCy, respectively, were used.

Enzyme activity assays—The assay and the calculation of β-galactosidase units (expressed as units per OD600) were carried out as described in Miller, J. H. (1982) *Experiments in Molecular Biology*, Cold Spring Harbor Laboratory Press, Cold Spring Harbor N.Y. Overnight cultures were diluted 100-fold in fresh medium and samples were taken at hourly intervals for OD600 readings and β-galactosidase activity determinations. Induction of the phosphate starvation response was monitored by alkaline phosphatase activity determinations as described in Hulett et al. (1990) *J. Bacteriol.* 172, 735-740.

As expected, upon a medium shift from high phosphate (HPDM) to low phosphate (LPDM) medium in order to induce a phosphate starvation response, tatCd transcription could be observed in *B. subtilis* ItatCd. In this strain, relatively low, but constant levels of β-galactosidase production were reached within a period of four hours after the change to LPDM medium, while no β-galactosidase production was detectable in the parental strain 168 (no lacZ gene fusion present; Table II). In contrast, when cells of *B. subtilis* ItatCd were grown in minimal (MM), sporulation (SSM) or trypton/yeast extract (TY) media, none of which induces a phosphate starvation response, no transcription of the tatCd gene was detectable; under these conditions, the β-galactosidase levels in cells of *B. subtilis* ItatCd were similar to those of the parental strain 168. Completely different results were obtained with *B. subtilis* ItatCy: the tatCy gene was transcribed in all growth media tested and, notably, the transcription of tatCy in LPDM medium was much higher than that of the tatCd gene (Table III). In contrast to the tatCd gene, the highest levels of tatCy transcription were observed in MM and TY medium, while the lowest levels of tatCy transcription were observed in SSM medium (Table III). In conclusion, these findings show that tatCd is only transcribed under conditions of phosphate starvation, in contrast to tatCy, which is transcribed under all conditions tested.

EXAMPLE 4

PhoD is not Transported in E. coli

Plasmids, bacterial strains and media—Table 5 lists the plasmids and bacterial strains used. TY medium (h-yptone/yeast extract) contained Bacto wiptone (1%), Bacto yeast extract (0.5%) and NaCl (1%). For pulse-chase labelling experiments M9-Minimal medium was prepared as described (Miller et al. (1992) Suppression of the growth and export defects of an *Escherichia coli* secA(Ts) mutant by a gene cloned from *Bacillus subtilis*. *Mol. Gen. Genet.* 235, 89-96). When required, media were supplemented with ampicillin (100 µg/ml), kanamycin (40 µg/ml), chloramphenicol (20 µg/ml), tetracycline (12.5 µg/ml), arabinose (0.2%), isopropyl-β-D-thiogalactopyranoside (IPTG; 100 µM), nigericin (1 µM) and/or sodium azide (3 mM). [35S]-Methionine was from Hartman Analytic (Braunschweig, Germany), [14C]-labelled molecular weight marker from Amersham International (Amersham, Bucks, U.K.).

DNA techniques—Procedures for DNA purification, restriction, ligation, agarose gel electrophoresis, and transformation of *E. coli* were carried out as described in Sambrook et al. Restriction enzymes were from MBI Fermentas. PCR (polymerase chain reaction) was carried out with the VENT DNA polymerase (New England Biolabs).

To construct pAR3phoD, the phoD gene including its ribosome binding site was amplified from the chromosome of *B. subtilis* strain 168 by PCR using the primers P1 (5'-GAG GAT CCA TGA GGA GAG AGG GGA TCT TGA ATG GCA TAC GAC-3') containing a BamHI site, and P2 (5'-CGA TCC TGC AGG ACC TCA TCG GAT TGC-3') containing a PstI site. The amplified fragment was cleaved with BamHI and PstI, and cloned in the corresponding sites of pAR3. The resulting plasmid pAR3phoD allowed the arabinose inducible expression of wild type phoD in *E. coli*.

To construct a gene fusion between bla and phoD genes, the signal sequence less phoD was amplified using primers P3 (5'-GTA GGA TCC GCG CCT AAC TTC TCA AGC-3') containing a BamHI site and primer P2 containing a PstI site. The amplified fragment was cleaved with BamHI and PstI, and cloned in the corresponding sites of pUC19, resulting in plasmid pUC19'phoD. Next, the 5' region of TEM-β-lactamase encoding its signal sequence was amplified from plasmid pBR322 by PCR with primers B1 (5'-ATA GAA TTC AAA AAG GAA GAG TAT G-3') containing an EcoRI site, and primer B2 (5'-CTG GGG ATC CAA AAA CAG GAA GGC-3') containing a BamHI site. The amplified PCR fragment was cleaved with BamHI and EcoRI and inserted into pUC19'phoD, cleaved with the same restriction enzymes, resulting in plasmid pUC19bla-phoD. For easy selection of recombinant clones plasmid pOR124, containing a tetracycline resistance gene was inserted 3' of the bla-phoD gene fusion using an unique PstI site. From the resulting plasmid pUC19bla-phoD-Tc an EcoRI-BglII fragment containing bla-phoD and the tetracycline resistance gene of pOR124 was isolated and inserted into pMUTIN2 cleaved with EcoRI and BamHI. At plasmid pMutin2bla-phoD the bla-phoD gene fusion is under control of the IPTG-inducible $P_{SPAC}$ promoter.

To construct a gene fusion consisting of the signal sequence of phoD and lacZ, a DNA fragment encoding the signal peptide of PhoD and the translational start site of phoD was amplified by PCR with primer P1 containing a BamHI site and primer P4 (5'-GAG AAG GTC GAC GCA GCA TTT ACT TCA AAG GCC CC-3') containing a SalI site, and inserted into the corresponding sites of pOR124 resulting in plasmid pOR124phoD'. Next the lacZ gene lacking nine 5' terminal codons was amplified using primers L1 (5'-ACC GGG TCG ACC GTC GTT TTA CAA CG-3') containing a SalI site and primer L2 (5'-GGG AAT TCA TGG CCT GCC CGG TT-3') containing an EcoRI site and subsequently inserted into the corresponding sites of pOR124phoD. The resulting plasmid pOR124phoD-lacZ was linearized with BamHI and inserted into pAR3 cleaved with BglII. The resulting plasmid pAR3phoD-lacZ allows the arabinose inducible expression of the phoD-lacZ gene fusion.

To obtain a plasmid mediating an inducible overexpression of $tatA_d tatC_d$ of *B. subtilis*, the DNA region containing these genes including their ribosome binding sites was amplified by PCR with the primers T1 (5'-CAA GGA TCC CGA ATT AAG GAG TGG-3') containing a BamHI site and primer T2 (5'-GGT CTG CAG CTG CAC TAA GCG GCC GCC-3') containing a PstI site. The amplified fragment was cleaved with BamHI and PstI and cloned into the corresponding sites of pQE9 (QIAGEN), resulting in pQE9tatA$_d$/C$_d$.

To obtain TG1 ΔtatABCDE, plasmids pFAT44 and subsequently PFAT126 covering in-frame deletions of *E. coli* tatE and tatABCD genes, respectively, were transferred to the chromosome of TG1 as described. Mutant strain TG1 ΔtatABCDE was verified phenotypically by mutant cell separation phenotype, hypersensitivity to SDS and resistance to P1 phages as described (Stanley et al. (2001) *Escherichia coli* strains blocked in Tat-dependent protein export exhibit pleiotropic defects in the cell envelope. *J. Bacteriol.* 183, 139-144).

SDS-PAGE and Western blot analysis—SDS-polyacrylamide gel electrophoresis (SDS-PAGE) was carried out as described by Laemmli (Laemmli, U.K. (1970) Cleavage of structural proteins during assembly of the head of bacteriophage T4. *Nature*, 227, 680-685). After separation by SDS-PAGE, proteins were transferred to a nitrocellulose membrane (Schleicher and Schiill) as described by Towbin et al. (Towbin et al. (1979) Electrophoretic transfer of proteins from polyacrylamide gels to nitrocellulose sheets: procedure and some applications. *Proc. Natl. Acad. Sci. USA*, 76, 4350-4354). Proteins were visualised using specific antibodies against PhoD (16), LacZ (5PRIME-3PRIME, Boulder, USA) and SecB (laboratory-collection) and alkaline phosphatase-conjugated goat anti-rabbit antibodies (SIGMA) according to the manufacturer's instructions.

Protein-chase experiments, immunoprecipitation and quantification of protein—Pulse-labelling experiments of *E. coli* strains were performed as described earlier (Mililer et al. (1992) Suppression of the growth and export defects of an *Escherichia coli* secA(Ts) mutant by a gene cloned from *Bacillus subtilis*. *Mol. Gen. Genet.* 235, 89-96). Cultures were pulse labelled with 100 µCi [$^{35}$S]-methionine, chased with unlabelled methionine and samples were taken at the times indicated immediately followed by precipitation with trichloracetic acid (0° C.). After cell lysis proteins were precipitated with specific antibodies against PhoD (Miller, J. P. and Wagner, M. (1999) Localisation of the cell wall-associated phosphodiesterase PhoD of *Bacillus subtilis*. *FEMS Microbiol. Lett.*, 180, 287-296) or β-lactamase and β-galactosidase (5PRIME-3PRIME, Boulder, USA). Relative amounts of radioactivity were estimated by using a Phospho-Imager (Fuji) and associated image analytical software PC-BAS.

In vivo protease mapping—In vivo protease mapping was carried out according to Kiefer et al. (*EMBO J.* (1997) 16, 2197-2204). For spheroplast formation, cells were grown in TY-medium to exponential growth. For induction of gene expression the medium was supplemented with arabinose (0.2%) and/or IPTG (1 mM) for 60 min. After spheroplast formation cells were treated with proteinase K (SIGMA), with proteinase K and Triton X-100 or remained untreated. Detection of cytosolic SecB revealed the proteinase K resistance of Triton X-100 untreated spheroplasts.

Determination of β-galactosidase activity—The assay and the calculation of β-galactosidase units (expressed as units per $OD_{600}$) were carried out as described by Miller ((1972) Experiments in molecular genetics. Cold Spring Harbor Laboratory, Cold Spring Harbor, N.Y.) using 2-Nitrophenyl-β-D-galactopyranoside (ONPG, Serva). Enzymatic activity of the supernatant of lysozyme treated spheroplasts reflected the periplasmic space. Activity associated to the spheroplasts represented the cytosolic and cytoplasms membrane bound activity.

PhoD is not transported in *E. coli*—The initial aim was to test whether PhoD could be exported by the Tat pathway in *E. coli*. For this purpose, we placed the encoding this peptide under the control of the $P_{BAD}$ promoter of *Salmonella typhimurium* localized at plasmid pAR3. The resulting plasmid allowed the arabinose-inducible enzymatically active production of PhoD in *E. coli* TG1 (data not shown). Since phosphodiesterase is highly toxic for the cell physiology of *E. coli* immediately after induction of phoD expression cell growth ceased. In order to quantify transport of PhoD in *E. coli* TG1 (pARphoD) pulse-chase experiments were performed. As shown in FIG. 8, no processing of the wild-type prePhoD was observed even after 60 min chase, indicating that prePhoD was not translocated by the *E. coli* Tat machinery. Localisation of PhoD was further localised by in vivo protease mapping. As shown in FIG. 8 prePhoD was not accessible to Proteinase K at the outer side of the cytosolic membrane, demonstrating that PhoD remains in a cytosolic localisation in *E. coli* TG1 (pARphoD).

PhoD can be transported via the Sec-dependent protein translocation pathway—Absence of prePhoD processing in *E. coli* could be due to inefficient recognition of the signal peptide of PhoD by the *E. coli* Tat-machinery or due to the nature of the mature part of the PhoD peptide. This *B. subtilis* protein could have unexpected folding characteristics or necessity of co-factors not present in *E. coli*. In order to address this question, the DNA encoding the mature peptide of PhoD was fused to the region encoding the signal peptide of TEM-β-lactamase ($SP_{Bla}$). The resulting gene fusion was cloned into the pMUTIN2 vector containing an IPTG-inducible $P_{SPAC}$ promoter allowing the synthesis of the $SP_{Bla}$-PhoD peptide. The transport and processing of this fusion protein was analysed by immunoblotting of whole cell extracts of *E. coli* strain TG1 (pMUTIN2bla-phoD). As shown in FIG. 8A, lane 2, $SP_{Bla}$-PhoD was completely converted to a protein with a molecular weight of mature PhoD indicating the efficient transport of the protein. In order to elucidate the export path used for $SP_{Bla}$-PhoD translocation, Sec-dependent transport was selectively inhibited by addition of sodium azide (3 mM). While presence of sodium-azide abolished conversion of $SP_{Bla}$-PhoD to PhoD addition of nigericin did not retard processing of $SP_{Bla}$-PhoD (FIG. 8A, lanes 3 and 4). To analyse Sec-dependence of $SP_{Bla}$-PhoD transport more detailed, expression of bla-phoD in *E. coli* TG1(pMUTIN2bla-phoD) was induced in presence or absence of sodium azide, pulse-labelled with [$^{35}$S]-methionine and PhoD was subsequently immunoprecipitated. FIG. 8B demonstrates the kinetics of conversion of $SP_{Bla}$-PhoD to mature PhoD. Presence of sodium azide significantly retarded maturation of $SP_{Bla}$-PhoD (FIG. 8C). These data indicate that PhoD can be transported in *E. coli* Sec-dependent. Thus, it can be concluded that the signal peptide less PhoD peptide is not canalising the export route and does not prevent efficient transport or processing.

The signal peptide of PhoD can not mediate transport of LacZ in *E. coli* wild type cells—It has been shown that signal peptides containing a twin arginine motif can canalise transport of heterologous proteins via the Tat-dependent translocation route (reviewed in Wu et al. (2000) Bacterial twin-arginine signal peptide-dependent protein translocation pathway: evolution and mechanism. *J. Mol. Microbiol. Biotechnol.* 2, 179-189). The signal peptide of the *E. coli* TMAO reductase (TorA) has been successfully used to mediate Tat-dependent transport of the thylakoidal protein 23K, the glucose-fructose oxidoreductase GFOR of *Zymomonas mobilis* and the green fluorescent protein GFP. Other reports indicated that Tat-signal peptides could determine the specificity of the Tat-dependent transport (Wu, supra). So could GFOR not be translocated in *E. coli* (28).

To test whether the signal peptide of PhoD is recognised by the *E. coli* Tat machinery and could canalise the transport of a protein in *E. coli*, we constructed a gene fusion consisting of the DNA region encoding the 56 amino acid residues of PhoD signal peptide ($SP_{PhoD}$) and the lacZ gene encoding β-galactosidase as a reporter protein. The gene hybrid was inserted into plasmid pAR3 resulting in plasmid pAR3phoD-lacZ. Induction of production of the $SP_{PhoD}$-LacZ fusion protein in *E. coli* TG1 resulted in LacZ$^+$ colonies (data not shown). Hence, correct folding and tetramerisation of the peptide as a prerequisite for its activity does occur in *E. coli*.

To analyse if the signal peptide of PhoD could mediate translocation of LacZ into an extracytosolic localisation, enzymatic activity of LacZ was monitored in *E. coli* TG1 (pAR3phoD-lacZ). As shown in table II the majority of LacZ activity remained in the cytosol or the cytosolic membrane. Since absence of enzymatic LacZ activity could be a result of inefficient folding rather than absence of transport, we next studied localisation of LacZ by using in vivo protease mapping. As shown in FIG. 9A no processing of $SP_{PhoD}$-LacZ could be observed. The $SP_{PhoD}$-LacZ fusion protein was not susceptible to protease digestion in spheroplasts. When spheroplasts were destroyed by addition of Triton X-100, the unprocessed $SP_{PhoD}$-LacZ protein became protease sensitive (FIG. 9A, lane 3). The reliability of the method was verified by using the cytosolic protein SecB as internal control (FIG. 9A). In spheroplasts SecB was resistant to proteinase K, but was digested after solubilising the spheroplasts with Triton X-100.

Export of $SP_{PhoD}$-LacZ fusion protein in *E. coli* needs presence of the *B. subtilis* TatA$_d$ and TatC$_d$ transport components.—The data demonstrated above indicate that the Tat system of *E. coli* does not mediate transport of prePhoD or of the $SP_{PhoD}$-LacZ fusion protein. Absence of translocation could be due to the necessity of additional components for the translocation of PhoD present only in *B. subtilis* or due to the specificity of recognition of PhoD as a Tat-dependent substrate. Our previous observation that only the TatC$_d$ protein but not the second copy of TatC could mediate the Tat-dependent transport in *B. subtilis* was a first indication for a specific recognition of prePhoD. To test this hypothesis, the *B. subtilis* tatA$_d$/C$_d$ gene pair was amplified from the chromosome of *B. subtilis* and inserted under the control of the IPTG-inducible promoter of pQE9 (QIAGEN). The resulting plasmid pQE9tatA$_d$/C$_d$ and the repressor plasmid pREP4 were transformed into *E. coli* TG1 (pARphoD) and TG1 (pARphoD-lacZ).

In order to study the effect of TatA$_d$/C$_d$ proteins on localisation of PhoD, strain TG1 (pARphoD, pREP4, pQE9tatA$_d$/

$C_d$) expression of phoD as well as tatA$_d$/C$_d$ was induced with arabinose and IPTG. Unexpectedly, no PhoD could be detected in strain TG1 (pARphoD, pREP4, pQE9tatA$_d$/C$_d$) using Western blotting (data not shown). Induction of TatA$_d$/C$_d$ proteins in strain TG1 (pARphoD, pREP4, pQE9tatA$_d$/C$_d$) resulted in stable co-production of TatA$_d$/C$_d$ proteins and the SP$_{PhoD}$-LacZ fusion protein (data not shown). SP$_{PhoD}$-LacZ processing was analysed in presence and absence of TatA$_d$/C$_d$ using pulse-chase labelling and subsequent immunoprecipitation with specific antibodies against LacZ. While in TG1 (pARphoD'-LacZ) no processing of SP$_{PhoD}$-LacZ could be observed (FIG. 10A), in strain TG1(pARphoD, pREP4, pQE9tatA$_d$/C$_d$) the peptide was at least partially processed (FIG. 10B).

Since processing of the translocation product is an indication of membrane translocation but does not necessarily prove that export of the protein has occurred, we examined whether LacZ could be localised in the periplasmic space in TG1 (pARphoD, pREP4, pQE9tatA$_d$/C$_d$). As shown in table II the relative amount of periplasmic LacZ activity was significantly raised when compared to TGI(pARphoD'-lacZ). Surprisingly, relative activity of LacZ in the strain expressing tatA$_d$/C$_d$ was much lower than compared to that of TG1 (pARphoD'-lacZ). To monitor localisation of the LacZ peptide, cells of strain TG1 (pARphoD, pREP4, pQE9tatA$_d$/C$_d$) were converted to spheroplasts, and treated with Proteinase K. As shown in FIG. 10B co-expressing tatA$_d$/C$_d$ the fusion protein SP$_{PhoD}$-LacZ was completely susceptible to protease digestion in spheroplasts. The resistance of SecB to the proteolytic digestion confirms the reliability of the method. Unexpectedly, both the processed form and the precursor of the fusion protein were accessible to the protease treatment. These results clearly show that the SP$_{PhoD}$-LacZ fusion protein is exported into the periplasmic space of E. coli when the B. subtilis tatA$_d$/C$_d$ genes are co-expressed.

Tat$_d$/C$_d$-mediated transport of SP$_{PhoD}$-LacZ needs delta pH dependent gradient at the cytosolic membrane and is Sec-independent—To directly proof that the membrane translocation of the system is dependent on the pH gradient across the cytosolic membrane, Sec- and Tat-dependent protein translocation pathways were selectively blocked. Nigericin, an ionophore inhibiting the Tat-dependent protein translocation as a result of destroying the membrane potential (29), did efficiently block both, processing and translocation of SP$_{PhoD}$-LacZ in TG1(pARphoD'-lacZ, pREP4, pQE9tatA$_d$/Cd) (FIG. 11A). Sodium azide (3 mM), which severely inhibits Sec-dependent protein export by interfering with the translocation-ATPase activity of the SecA protein. (30), did not affect the localisation and the processing of the SP$_{PhoD}$-LacZ fusion protein in this strain as shown in FIG. 11B.

TatA$_d$/C$_d$-mediated transport of SP$_{PhoD}$-LacZ is not assisted by E. coli Tat components—Despite the above observations it can not be excluded that the E. coli Tat machinery assists TatA$_d$/C$_d$-mediated transport of SP$_{PhoD}$-LacZ. The E. coli tat genes are constitutively expressed in E. coli and therefore form a functional constitutive translocase unit (Jack et al. (2001) Constitutive expression of Escherichia coli tat genes indicates an important role for the twin-arginine translocase during aerobic and anaerobic growth. J. Bacteriol. 183, 1801-1804). To exclude co-operative action of B. subtilis and E. coli Tat proteins, E. coli strain TG1 was deleted for tatABCDE genes and subsequently transformed with plasmids pARphoD'-lacZ, pREP4 and QE9tatA$_d$/C$_d$. Processing and localisation of the SP$_{PhoD}$-LacZ fusion protein was analysed under identical conditions as described for the E. coli tat+ strain. Despite the fact that the total amount of LacZ found in the periplasmic fraction was reduced than compared to the E. coli tat wild type strain expressing phoD'-LacZ and tatA$_d$/C$_d$, the relative amount of periplasmic LacZ was significantly elevated than compared to TG1(pARphoD'-LacZ) (Table II). As shown in FIG. 12 in absence of the E. coli tatABCDE genes most of the SP$_{PhoD}$-LacZ hybrid protein was protease accessible demonstrating the extracytosolic localisation of SP$_{PhoD}$-LacZ. The resistance of SecB to the proteolytic digestion demonstrated the stability of the spheroplasts (FIG. 13). Surprisingly, no processing of the SP$_{PhoD}$-LacZ fusion protein could be observed in absence of tatABCDE. Taken together, the B. subtilis Tat components TatAd/Cd can mediate translocation of the hybrid peptide consisting of the twin-arginine signal peptide of PhoD and LacZ.

Although the foregoing invention has been described in some detail by way of illustration and example for purposes of clarity and understanding, it will be obvious that certain changes and modifications may be practiced within the scope of the appended claims.

TABLE I

Predicted Twin-Arginine Signal Peptides of B. subtilis*

| protein | signal peptide |
| --- | --- |
| AlbB | MSPAQRRILLY................AIAILF |
| AmyX[TM] | MVSIRRSFE................EQKEIM |
| AppB[TM] | MAAYIIRRT................KAAPG |
| LipA | MKFVKRR................QPSAKAAEH |
| OppB[TM] | MLKYIGRR................QAAPG |
| PbpX | MTSPTRRRTAKRRRRKLNKR................WNALHR |
| PhoD | MAYDSRFDEWVQKLKEESFQNNTFDRRKFIQ................VGAFEV |
| QcrA | MGGKHDISRRQFLN................RFA |
| SpoIIIJ | MLLKRR................LAGCSSV |
| TlpA[TM] | MKKTLTTIRRSSIARR................QS |

TABLE I-continued

Predicted Twin-Arginine Signal Peptides of *B. subtilis*\*

| protein | signal peptide |
|---|---|
| WapA | MKKRKRRNFKR▓▓▓▓▓▓▓▓▓▓▓▓▓▓▓▓▓▓▓▓D<u>VLA</u>KST |
| WprA | MKRRKFSS▓▓▓▓▓▓▓▓▓▓▓▓▓▓▓▓▓▓▓▓▓TK<u>AAA</u>AGA |
| YceA[TM] | MEMFDLEFMRR▓▓▓▓▓▓▓▓▓▓▓▓▓▓▓▓▓▓▓▓▓▓*RR*Q |
| YdeJ | MKKRRK▓▓▓▓▓▓▓▓▓▓▓▓▓▓▓▓▓▓▓▓LAGCTDS |
| YdhF | MRR▓▓▓▓▓▓▓▓▓▓▓▓▓LAGCSSN |
| YdhK | MSAGKSYRKKMKQRRMNMKISK▓▓▓▓▓▓▓▓▓▓▓▓▓▓▓LSACGNNN |
| YesM[TM] | MKKRVAGWYRRMKIKDK▓▓▓▓▓▓▓▓▓▓▓▓▓▓▓▓▓▓▓▓<u>QYA</u>FHV |
| YesW | MRRSCLMIRRRKR▓▓▓▓▓▓▓▓▓▓▓▓▓▓▓▓▓▓<u>VKA</u>EGA |
| YfkN[TM] | MRIQKRRTHVENILR▓▓▓▓▓▓▓▓▓▓▓▓▓▓▓▓▓▓▓<u>IHA</u>EES |
| YkpC | MLRDLGRR▓▓▓▓▓▓▓▓▓▓▓▓▓▓▓▓<u>SLA</u>NMP |
| YkuE | MKKMSRRQFLK▓▓▓▓▓▓▓▓▓▓▓▓▓▓▓▓▓▓<u>GYA</u>RYL |
| YmaC | MRRFLLN▓▓▓▓▓▓▓▓▓▓▓▓▓▓▓▓▓H<u>YSL</u>EPE |
| YmzC | MFESEAELRR▓▓▓▓▓▓▓▓▓▓▓▓▓▓LFGACGN |
| YubF[TM] | MQKYRRRNT▓▓▓▓▓▓▓▓▓▓▓▓▓▓▓▓▓▓▓▓▓NADNL |
| YuiC[TM] | MMLNMIRR▓▓▓▓▓▓▓▓▓▓▓▓▓▓▓▓▓▓IEAKDL |
| YvhJ | MAERVRVRVRKKKKSKRRKILKR▓▓▓▓▓▓▓▓▓▓▓▓▓▓▓▓KLY |
| YwbN | MSDEQKKPEQIHRRDILK▓▓▓▓▓▓▓▓▓▓▓▓▓▓▓▓▓▓▓<u>QTA</u>AKP |

\*Putative twin-arginine signal peptides were identified in two ways. First, the presence of the consensus sequence R-R-X-ϕ-ϕ (ϕ is a hydrophobic residue), immediately in front of an amino-terminal hydrophobic region as predicted with the TopPred2 algorithm (34, 35), was determined. To this purpose, the first 60 residues of all annotated proteins of *B. subtilis* in the SubtiList database (http://bioweb.pasteur.fr/Genolist/Subtilist.html) were used. Second, within the group of twin-arginine membrane sorting signals, cleavable signal peptides were identified with the SignalP algorithm (61, 62). Conserved residues of the twin-arginine consensus sequence (R-R-X-ϕ-ϕ) are indicated in bold. In addition, positively charged residues that could function as a so-called Sec-avoidance signal (54) are indicated in bold and italics. The hydrophobic H-domain is indicated in gray shading. In signal peptides with a predicted signal peptidase I cleavage site, residues from position −3 to −1 relative to the signal peptidase I cleavage site are underlined. Notably, some of these proteins contain one or more putative transmembrane segments elsewhere in the protein (indicated with "TM"), or are putative lipoproteins. Residues forming a so-called lipobox for signal peptidase II cleavage are enlarged in size.

TABLE II

Plasmids and Strains

| | Relevant properties | Reference |
|---|---|---|
| Plasmids | | |
| pUC21 | cloning vector; 3.2 kb; Ap$^r$ | 63 |
| pJCd1 | pUC21 derivative; carrying the tatCd gene; 5.4 kb; Ap$^r$ | This work |
| pJCd2 | pUC21 derivative for the disruption of tatCd; 6.3 kb; Ap$^r$; Km$^r$ | This work |
| pJCy1 | pUC21 derivative; carrying the tatCy gene; 5.3 kb; Ap$^r$ | This work |
| pJCy2 | pUC21 derivative for the disruption of tatCy; 6.5 kb; Ap$^r$; Sp$^r$ | This work |
| pMutin2 | pBR322-based integration vector for *B. subtilis*; containing a multiple cloning site downstream of the Pspac promoter, and a promoter-less lacZ-gene preceded by the RBS of the spoVG gene; 8.6 kb; Ap$^r$; Em$^r$ | 31 |
| pM1Cd1 | pMutin2 derivative; carrying the 5' part of the *B. subtilis* tatCd gene | This work |
| pM1Cy1 | pMutin2 derivative; carrying the 5' part of the *B. subtilis* tatCy gene | This work |
| pDG792 | contains a Km resistance cassette; 4.0 kb; Ap$^r$, Km$^r$ | 64 |
| pDG1726 | contains a Sp resistance cassette; 3.9 kb; Ap$^r$, Sp$^r$ | 64 |
| Strains | | |
| *E. coli* | | |
| MC1061 | F$^-$; araD139; Δ (ara-leu)7696; Δ (lac)X74; galU; galK; hsdR2; mcrA; mcrB1; rspL | 65 |
| *B. subtilis* | | |
| 168 | trpC2 | 2 |
| ΔtatCd | trpC2; tatCd; Km$^r$ | This work |
| ΔtatCy | trpC2; tatCy; Sp$^r$ | This work |
| ItatCd | trpC2; Pspac-tatCd; tatCd-lacZ; Em$^r$ | This work |
| ItatCy | trpC2; Pspac-tatCy; tatCy-lacZ; Em$^r$ | This work |
| ΔtatCd-ΔtatCy | trpC2; tatCd; Km$^r$; tatCy; Sp$^r$ | This work |
| ItatCd-ΔtatCy | trpC2; Pspac-tatCd; tatCd-lacZ; Em$^r$; tatCy; Sp$^r$ | This work |

TABLE III

β-galactosidase activity (U/OD$_{600}$)*.

| strain | LPDM | MM | SSM | TY |
|---|---|---|---|---|
| 168 | 0 | 0.1 ± 0.1 | 0.3 ± 0.2 | 0.6 ± 0.2 |
| ItatCd | 1.1 ± 0.7 | 0.1 ± 0.1 | 0.3 ± 0.2 | 0.5 ± 0.2 |
| ItatCy | 6.1 ± 2.5 | 10.0 ± 3.6 | 4.0 ± 2.0 | 13.2 ± 5.5 |

*To investigate the transcription of the tatCd and tatCy genes, cells of B. subtilis ItatCd (tatCd-lacZ), ItatCy (tatCy-lacZ) or the parental strain 168 (no lacZ gene fusion) were grown for 10 hours in LPDM, MM, SSM or TY medium after dilution from an overnight culture. Samples for β-galactosidase activity determinations were taken at hourly intervals, starting 4 hours after dilution from the overnight culture. As the β-galactosidase activities showed little variation during the entire period of sampling, average values were determined. The numbers in the table represent average values from 3 different experiments. Note that HPDM medium was used for the overnight culture of cells grown in LPDM medium, while overnight cultures of cells grown in MM, SSM or TY medium were prepared with the respective media.

TABLE IV

Twin-Arginine Signal Peptides of PhoD and PhoD-like proteins*

| protein | signal peptide |
|---|---|
| PhoD (Bsu) | MAYDSRFDEWVQKLKEESFQNNTFDRRKFIQ▓▓▓▓▓▓▓▓▓▓▓▓▓▓▓▓▓▓▓▓<u>VGA</u>FEV |
| SP1 (Sco) | MTPANHQAPTSAPSPAPSQSSHAPELRAAARSLGRRRFLT▓▓▓▓▓▓▓▓▓▓▓▓▓▓T<u>ASA</u>AEL |
| SP2 (Sco) | MAPTGRPSALAEHAFSPHDAVLGAAARHLGRRRFLT▓▓▓▓▓▓▓▓▓▓▓▓▓▓<u>AVA</u>APE |
| SP3 (Sco) | MTSRHRASENSRTPSRRTVVK▓▓▓▓▓▓▓▓▓▓▓▓▓▓<u>ADA</u>APA |
| SP4 (Ste) | MTPAARPSQHAPELRAAARHLGRRRFLT▓▓▓▓▓▓▓▓▓▓▓▓▓▓T<u>AAA</u>AEL |

*Homologues of B. subtilis PhoD were identified by amino acid sequence similarity searches in GenBank using the BLAST algorithm. SP1 (Sco), gene SCC75A.32c of Streptomyces coelicolor (CAB61732); SP2 (Sco), gene SCF43A.18 of S. coelicolor (CAB48905); SP3 (Sco), gene SC4G6.37 of S. coelicolor (CAB51460), and SP4, phoD gene of Streptomyces tendae (CAB62565). GenBank accession numbers are indicated in parentheses. Conserved residues of the twin-arginine consensus sequence are indicated in bold. The hydrophobic H-region is indicated in in gray shading. Signal peptidase I recognition sequences predicted with the SignalP algorithm (61, 62) are underlined.

TABLE 5

Plasmids and Strains

| | Relevant properties | Reference |
|---|---|---|
| Plasmids | | |
| pAR3 | pACYC184 derived plasmid carrying the araB promoter operator and the araC repressor gene from Salmonella typhimurium; Cm$^{ra}$ | 25 |
| pAR3phoD | pAR3 derivative; carrying the phoD gene; Cm$^r$ | This work |
| pAR3phoD-lacZ | pAR3 derivative; carrying a fusion gene consisting of the signal sequence region of phoD and lacZ; Cm$^r$ | This work |
| pQE9 | pBR322-based vector for IPTG-inducible synthesis of His$_6$-tagged proteins; Ap$^r$ | Qiagen |
| pREP4 | plasmid; containing lacI$^q$ repressor gene; Km$^r$ | Qiagen |
| pORI24 | plasmid; replicates only in E. coli rep$^+$ strains; Tc$^r$ | 37 |
| pMUTIN2 | pBR322-based integration vector for B. subtilis; containing a multiple cloning site downstream of the Pspac promoter, and a promoter-less lacZ-gene preceded by the RBS of the spoVG gene; Ap$^r$; Em$^r$ | 38 |
| pMUTIN2bla-phoD | PMUTIN2 derivative; carrying a fusion gene consisting of signal sequence region of bla and phoD | This work |
| pQE9tatA$_d$/C$_d$ | pQE9 derivative; carrying the B. subtilis tatA$_d$/C$_d$ genes | This work |
| pFAT44 | pMAK705 (Hamilton et al., 1989) derivative plasmid containing in frame deletion of E. coli tatE | 7 |
| pFAT126 | pMAK705 derivative plasmid containing in frame deletion of E. coli tatABCD | 39 |

TABLE 5-continued

Plasmids and Strains

| | Relevant properties | Reference |
|---|---|---|
| Strains | | |
| *E. coli* | | |
| TG1 | F⁻ araD139 Δ(ara-leu)7696 Δ (lac)X74 galU galK hsdR2 mcrA mcrB1 rspL | 40 |
| TG1 ΔtatABCE | TG1 ΔtatABCE | This work |
| *B. subtilis* | | |
| 168 | trpC2 | 13 |

$^a$Cm$^r$, chloramphenicol resistance marker; Ap$^r$, ampicillin resistance marker; Km$^r$, kanamycin resistance marker; Tc$^r$, tetracycline resistance marker; Em$^r$, erythromycin resistance marker

TABLE 6

Localisation of β-galactosidase activity in *E. coli* TG1(pAR3phoD-lacZ) strains.

| | LacZ activity (units/OD$_{600}$) | | | |
|---|---|---|---|---|
| strain | cell bound | periplasmic | total activity | % export |
| TG1(pAR3phoD-lacZ) | 1108 +/− 201 | 67 +/− 5 | 1175 | 6.4 +/− 3.4 |
| TG1(pAR3phoD-lacZ, pREP4, pQE9tatA$_d$/C$_d$) | 226 +/− 11 | 94 +/− 2 | 320 | 29.4 +/− 0.4 |
| TG1 ΔtatABCE (pAR3phoD-lacZ, pREP4, pQE9tatA$_d$/C$_d$) | 278 +/− 8 | 39 +/− 5 | 317 | 12.5 +/− 0.9 |

To investigate the translocation of the hybrid protein consisting of SP$_{PhoD}$ and LacZ, cells of *E. coli* strains were grown in TY medium to exponential growth.
Samples for β-galactosidase activity determinations were taken from supernatants of lysozyme treated cells representing periplasmic activity and spheroplasts representing cell bound activity.
Experiments were carried out with duplicated cultures.
+/−, standard deviation.

---

What is claimed is:

1. An isolated chimeric polypeptide comprising (i) a *Bacillus subtilis* LipA secretion signal peptide and (ii) a heterologous polypeptide.

2. The chimeric polypeptide of claim 1, wherein said heterologous polypeptide is not naturally associated with a secretion signal peptide.

3. The chimeric polypeptide of claim 1, wherein the heterologous polypeptide is an enzyme.

4. The chimeric polypeptide of claim 3, wherein the enzyme is selected from the group consisting of a protease, cellulase, amylase, lipase, and hydrolase.

5. The chimeric polypeptide of claim 4, wherein the enzyme is a protease.

6. The chimeric polypeptide of claim 4, wherein the enzyme is a cellulase.

7. The chimeric polypeptide of claim 4, wherein the enzyme is an amylase.

8. The chimeric polypeptide of claim 4, wherein the enzyme is a lipase.

9. The chimeric polypeptide of claim 4, wherein the enzyme is a hydrolase.

10. The chimeric polypeptide of claim 2, wherein the heterologous polypeptide is an enzyme.

11. The chimeric polypeptide of claim 10, wherein the enzyme is selected from the group consisting of a protease, cellulase, amylase, lipase, and hydrolase.

12. The chimeric polypeptide of claim 11, wherein the enzyme is a protease.

13. The chimeric polypeptide of claim 11, wherein the enzyme is a cellulase.

14. The chimeric polypeptide of claim 11, wherein the enzyme is an amylase.

15. The chimeric polypeptide of claim 11, wherein the enzyme is a lipase.

16. The chimeric polypeptide of claim 11, wherein the enzyme is a hydrolase.

* * * * *

SEQUENCE LISTING

<160> NUMBER OF SEQ ID NOS: 86

<210> SEQ ID NO 1
<211> LENGTH: 89
<212> TYPE: PRT
<213> ORGANISM: Escherichia coli

<400> SEQUENCE: 1

Met Gly Gly Ile Ser Ile Trp Gln Leu Leu Ile Ile Ala Val Ile Val
1               5                   10                  15

Val Leu Leu Phe Gly Thr Lys Lys Leu Gly Ser Ile Gly Ser Asp Leu
            20                  25                  30

Gly Ala Ser Ile Lys Gly Phe Lys Lys Ala Met Ser Asp Asp Glu Pro
        35                  40                  45

Lys Gln Asp Lys Thr Ser Gln Asp Ala Asp Phe Thr Ala Lys Thr Ile
    50                  55                  60

Ala Asp Lys Gln Ala Asp Thr Asn Gln Glu Gln Ala Lys Thr Glu Asp
65                  70                  75                  80

Ala Lys Arg His Asp Lys Glu Gln Val
                85

<210> SEQ ID NO 2
<211> LENGTH: 67
<212> TYPE: PRT
<213> ORGANISM: Escherichia coli

<400> SEQUENCE: 2

```
Met Gly Glu Ile Ser Ile Thr Lys Leu Leu Val Val Ala Ala Leu Val
1               5                   10                  15

Val Leu Leu Phe Gly Thr Lys Lys Leu Arg Thr Leu Gly Gly Asp Leu
                20                  25                  30

Gly Ala Ala Ile Lys Gly Phe Lys Ala Met Asn Asp Asp Asp Ala
            35                  40                  45

Ala Ala Lys Lys Gly Ala Asp Val Asp Leu Gln Ala Glu Lys Leu Ser
    50                  55                  60

His Lys Glu
65
```

<210> SEQ ID NO 3
<211> LENGTH: 57
<212> TYPE: PRT
<213> ORGANISM: Bacillus subtilis

<400> SEQUENCE: 3

```
Met Pro Ile Gly Pro Gly Ser Leu Ala Val Ile Ala Ile Val Ala Leu
1               5                   10                  15

Ile Ile Phe Gly Pro Lys Lys Leu Pro Glu Leu Gly Lys Ala Ala Gly
                20                  25                  30

Asp Thr Leu Arg Glu Phe Lys Asn Ala Thr Lys Gly Leu Thr Ser Asp
            35                  40                  45

Glu Glu Glu Lys Lys Lys Glu Asp Gln
    50                  55
```

<210> SEQ ID NO 4
<211> LENGTH: 70
<212> TYPE: PRT
<213> ORGANISM: Bacillus subtilis

<400> SEQUENCE: 4

```
Met Phe Ser Asn Ile Gly Ile Pro Gly Leu Ile Leu Ile Phe Val Ile
1               5                   10                  15

Ala Ile Ile Ile Phe Gly Pro Ser Lys Leu Pro Glu Ile Gly Arg Ala
                20                  25                  30

Ala Lys Arg Thr Leu Leu Glu Phe Lys Ser Ala Thr Lys Ser Leu Val
            35                  40                  45

Ser Gly Asp Glu Lys Glu Lys Ser Ala Glu Leu Thr Ala Val Lys
    50                  55                  60

Gln Asp Lys Asn Ala Gly
65                  70
```

<210> SEQ ID NO 5
<211> LENGTH: 62
<212> TYPE: PRT
<213> ORGANISM: Bacillus subtilis

<400> SEQUENCE: 5

```
Met Glu Leu Ser Phe Thr Lys Ile Leu Val Ile Leu Phe Val Gly Phe
1               5                   10                  15

Leu Val Phe Gly Pro Asp Lys Leu Pro Ala Leu Gly Arg Ala Ala Gly
                20                  25                  30

Lys Ala Leu Ser Glu Phe Lys Gln Ala Thr Ser Gly Leu Thr Gln Asp
            35                  40                  45

Ile Arg Lys Asn Asp Ser Glu Asn Lys Glu Asp Lys Gln Met
    50                  55                  60
```

<210> SEQ ID NO 6
<211> LENGTH: 171
<212> TYPE: PRT
<213> ORGANISM: Escherichia coli

<400> SEQUENCE: 6

Met Phe Asp Ile Gly Phe Ser Glu Leu Leu Leu Val Phe Ile Ile Gly
1               5                   10                  15

Leu Val Leu Gly Pro Gln Arg Leu Pro Val Ala Val Lys Thr Val
            20                  25                  30

Ala Gly Trp Ile Arg Ala Leu Arg Ser Leu Ala Thr Thr Val Gln Asn
        35                  40                  45

Glu Leu Thr Gln Glu Leu Lys Leu Gln Glu Phe Gln Asp Ser Leu Lys
    50                  55                  60

Lys Val Glu Lys Ala Ser Leu Thr Asn Leu Thr Pro Glu Leu Lys Ala
65                  70                  75                  80

Ser Met Asp Glu Leu Arg Gln Ala Ala Glu Ser Met Lys Arg Ser Tyr
                85                  90                  95

Val Ala Asn Asp Pro Glu Lys Ala Ser Asp Glu Ala His Thr Ile His
            100                 105                 110

Asn Pro Val Val Lys Asp Asn Glu Ala Ala His Glu Gly Val Thr Pro
        115                 120                 125

Ala Ala Ala Gln Thr Gln Ala Ser Ser Pro Glu Gln Lys Pro Glu Thr
    130                 135                 140

Thr Pro Glu Pro Val Val Lys Pro Ala Ala Asp Ala Glu Pro Lys Thr
145                 150                 155                 160

Ala Ala Pro Ser Pro Ser Ser Asp Lys Pro
                165                 170

<210> SEQ ID NO 7
<211> LENGTH: 258
<212> TYPE: PRT
<213> ORGANISM: Escherichia coli

<400> SEQUENCE: 7

Met Ser Val Glu Asp Thr Gln Pro Leu Ile Thr His Leu Ile Glu Leu
1               5                   10                  15

Arg Lys Arg Leu Leu Asn Cys Ile Ile Ala Val Ile Val Ile Phe Leu
            20                  25                  30

Cys Leu Val Tyr Phe Ala Asn Asp Ile Tyr His Leu Val Ser Ala Pro
        35                  40                  45

Leu Ile Lys Gln Leu Pro Gln Gly Ser Thr Met Ile Ala Thr Asp Val
    50                  55                  60

Ala Ser Pro Phe Phe Thr Pro Ile Lys Leu Thr Phe Met Val Ser Leu
65                  70                  75                  80

Ile Leu Ser Ala Pro Val Ile Leu Tyr Gln Val Trp Ala Phe Ile Ala
                85                  90                  95

Pro Ala Leu Tyr Lys His Glu Arg Arg Leu Val Pro Leu Leu Val
            100                 105                 110

Ser Ser Ser Leu Leu Phe Tyr Ile Gly Met Ala Phe Ala Tyr Phe Val
        115                 120                 125

Val Phe Pro Leu Ala Phe Gly Phe Leu Ala Asn Thr Ala Pro Glu Gly
    130                 135                 140

Val Gln Val Ser Thr Asp Ile Ala Ser Tyr Leu Ser Phe Val Met Ala
145                 150                 155                 160

Leu Phe Met Ala Phe Gly Val Ser Phe Glu Val Pro Val Ala Ile Val

-continued

```
                165                 170                 175
Leu Leu Cys Trp Met Gly Ile Thr Ser Pro Glu Asp Leu Arg Lys Lys
            180                 185                 190

Arg Pro Tyr Val Leu Val Gly Ala Phe Val Val Gly Met Leu Leu Thr
        195                 200                 205

Pro Pro Asp Val Phe Ser Gln Thr Leu Leu Ala Ile Pro Met Tyr Cys
    210                 215                 220

Leu Phe Glu Ile Gly Val Phe Phe Ser Arg Phe Tyr Val Gly Lys Gly
225                 230                 235                 240

Arg Asn Arg Glu Glu Asn Asp Ala Glu Ala Glu Ser Glu Lys Thr
            245                 250                 255

Glu Glu

<210> SEQ ID NO 8
<211> LENGTH: 254
<212> TYPE: PRT
<213> ORGANISM: Bacillus subtilis

<400> SEQUENCE: 8

Met Thr Arg Met Lys Val Asn Gln Met Ser Leu Leu Glu His Ile Ala
  1               5                  10                  15

Glu Leu Arg Lys Arg Leu Leu Ile Val Ala Leu Ala Phe Val Val Phe
            20                  25                  30

Phe Ile Ala Gly Phe Phe Leu Ala Lys Pro Ile Ile Val Tyr Leu Gln
        35                  40                  45

Glu Thr Asp Glu Ala Lys Gln Leu Thr Leu Asn Ala Phe Asn Leu Thr
    50                  55                  60

Asp Pro Leu Tyr Val Phe Met Gln Phe Ala Phe Ile Ile Gly Ile Val
 65                  70                  75                  80

Leu Thr Ser Pro Val Ile Leu Tyr Gln Leu Trp Ala Phe Val Ser Pro
                85                  90                  95

Gly Leu Tyr Glu Lys Glu Arg Lys Val Thr Leu Ser Tyr Ile Pro Val
            100                 105                 110

Ser Ile Leu Leu Phe Leu Ala Gly Leu Ser Phe Ser Tyr Tyr Ile Leu
        115                 120                 125

Phe Pro Phe Val Val Asp Phe Met Lys Arg Ile Ser Gln Asp Leu Asn
    130                 135                 140

Val Asn Gln Val Ile Gly Ile Asn Glu Tyr Phe His Phe Leu Leu Gln
145                 150                 155                 160

Leu Thr Ile Pro Phe Gly Leu Leu Phe Gln Met Pro Val Ile Leu Met
                165                 170                 175

Phe Leu Thr Arg Leu Gly Ile Val Thr Pro Met Phe Leu Ala Lys Ile
            180                 185                 190

Arg Lys Tyr Ala Tyr Phe Thr Leu Leu Val Ile Ala Ala Leu Ile Thr
        195                 200                 205

Pro Pro Glu Leu Leu Ser His Met Met Val Thr Val Pro Leu Leu Ile
    210                 215                 220

Leu Tyr Glu Ile Ser Ile Leu Ile Ser Lys Ala Ala Tyr Arg Lys Ala
225                 230                 235                 240

Gln Lys Ser Ser Ala Ala Asp Arg Asp Val Ser Ser Gly Gln
                245                 250

<210> SEQ ID NO 9
<211> LENGTH: 245
<212> TYPE: PRT
```

<213> ORGANISM: Bacillus subtilis

<400> SEQUENCE: 9

```
Met Asp Lys Lys Glu Thr His Leu Ile Gly His Leu Glu Glu Leu Arg
1               5                   10                  15

Arg Arg Ile Ile Val Thr Leu Ala Ala Phe Phe Leu Phe Leu Ile Thr
            20                  25                  30

Ala Phe Leu Phe Val Gln Asp Ile Tyr Asp Trp Leu Ile Arg Asp Leu
        35                  40                  45

Asp Gly Lys Leu Ala Val Leu Gly Pro Ser Glu Ile Leu Trp Val Tyr
    50                  55                  60

Met Met Leu Ser Gly Ile Cys Ala Ile Ala Ala Ser Ile Pro Val Ala
65                  70                  75                  80

Ala Tyr Gln Leu Trp Arg Phe Val Ala Pro Ala Leu Thr Lys Thr Glu
                85                  90                  95

Arg Lys Val Thr Ile Met Tyr Ile Met Tyr Ile Pro Gly Leu Phe Ala
            100                 105                 110

Leu Phe Leu Ala Gly Ile Ser Phe Gly Tyr Phe Val Leu Phe Pro Ile
        115                 120                 125

Val Leu Ser Phe Leu Thr His Leu Ser Ser Gly His Phe Glu Thr Met
    130                 135                 140

Phe Thr Ala Asp Arg Tyr Phe Arg Phe Met Val Asn Leu Ser Leu Pro
145                 150                 155                 160

Phe Gly Phe Leu Phe Glu Met Pro Leu Val Val Met Phe Leu Thr Arg
                165                 170                 175

Leu Gly Ile Leu Asn Pro Tyr Arg Leu Ala Lys Ala Arg Lys Leu Ser
            180                 185                 190

Tyr Phe Leu Leu Ile Val Val Ser Ile Leu Ile Thr Pro Pro Asp Phe
        195                 200                 205

Ile Ser Asp Phe Leu Val Met Ile Pro Leu Leu Val Leu Phe Glu Val
    210                 215                 220

Ser Val Thr Leu Ser Ala Phe Val Tyr Lys Lys Arg Met Arg Glu Glu
225                 230                 235                 240

Thr Ala Ala Ala Ala
                245
```

<210> SEQ ID NO 10
<211> LENGTH: 63
<212> TYPE: PRT
<213> ORGANISM: Bacillus alcalophilus

<400> SEQUENCE: 10

```
Met Gly Gly Leu Ser Val Gly Ser Val Val Leu Ile Ala Leu Val Ala
1               5                   10                  15

Leu Leu Ile Phe Gly Pro Lys Lys Leu Pro Glu Leu Gly Lys Ala Ala
            20                  25                  30

Gly Ser Thr Leu Arg Glu Phe Lys Asn Ala Thr Lys Gly Leu Ala Asp
        35                  40                  45

Asp Asp Asp Asp Thr Lys Ser Thr Asn Val Gln Lys Glu Lys Ala
    50                  55                  60
```

<210> SEQ ID NO 11
<211> LENGTH: 272
<212> TYPE: PRT
<213> ORGANISM: Bacillus alcalophilus

<400> SEQUENCE: 11

```
Met Thr Met Met Thr Pro Asn Gln Gln Thr Ser Lys Lys Lys Arg
 1               5                   10                  15

Lys Gly Arg Lys Gly Arg Val Pro Met Gln Asp Met Ser Ile Met Asp
             20                  25                  30

His Ala Glu Glu Leu Arg Arg Arg Ile Phe Val Val Leu Ala Phe Phe
         35                  40                  45

Ile Val Ala Leu Ile Gly Gly Phe Phe Leu Ala Val Pro Val Ile Thr
     50                  55                  60

Phe Leu Gln Asn Ser Pro Gln Ala Ala Asp Met Pro Phe Asn Ala Phe
65                  70                  75                  80

Arg Leu Thr Asp Pro Leu Arg Val Tyr Met Asn Phe Ala Val Ile Thr
                 85                  90                  95

Ala Leu Val Leu Ile Ile Pro Val Ile Leu Tyr Gln Leu Trp Ala Phe
            100                 105                 110

Val Ser Pro Gly Leu Lys Glu Asn Glu Gln Lys Ala Thr Leu Ala Tyr
            115                 120                 125

Ile Pro Ile Ala Phe Leu Leu Phe Leu Ala Gly Ile Ala Phe Ser Tyr
    130                 135                 140

Phe Ile Leu Leu Pro Phe Val Ile Ser Phe Met Gly Gln Met Ala Asp
145                 150                 155                 160

Arg Leu Glu Ile Asn Glu Met Tyr Gly Ile Asn Glu Tyr Phe Ser Phe
                165                 170                 175

Leu Phe Gln Leu Thr Ile Pro Phe Gly Leu Leu Phe Gln Leu Pro Val
            180                 185                 190

Val Val Met Phe Leu Thr Arg Leu Gly Val Val Thr Pro Thr Phe Leu
            195                 200                 205

Arg Lys Ile Arg Lys Tyr Ala Tyr Phe Ala Leu Leu Val Ile Ala Gly
    210                 215                 220

Ile Ile Thr Pro Pro Glu Leu Thr Ser His Leu Phe Val Thr Val Pro
225                 230                 235                 240

Met Leu Ile Leu Tyr Glu Ile Ser Ile Thr Ile Ser Ala Ile Thr Tyr
                245                 250                 255

Arg Lys Tyr His Gly Thr Thr Asp His Asn Gly Gln Glu Ser Ala Lys
            260                 265                 270
```

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
cccaagctta tgaaagggag ggcttttttg aatgg                35

<210> SEQ ID NO 13
<211> LENGTH: 26
<212> TYPE: DNA
<213> ORGANISM: Artificial Sequence
<220> FEATURE:
<223> OTHER INFORMATION: primer

<400> SEQUENCE: 13
gcggatccaa agctgagcac gatcgg                          26

<210> SEQ ID NO 14
<211> LENGTH: 39

```
<212> TYPE: DNA
<213> ORGANISM: Artificial Sequence
<220> FEATURE:
<223> OTHER INFORMATION: primer

<400> SEQUENCE: 14
cccaagctta aaagaaaga agatcagtaa gttaggatg                              39

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
gcggatccaa gtcctgagaa atccg                                           25

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
ggaattcgtg ggacggctac c                                               21

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
cgggatccat catgggaagc g                                               21

<210> SEQ ID NO 18
<211> LENGTH: 26
<212> TYPE: DNA
<213> ORGANISM: Artificial Sequence
<220> FEATURE:
<223> OTHER INFORMATION: primer

<400> SEQUENCE: 18
ggggtaccgg aaaacgcttg atcagg                                          26

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
cgggatcctt tgggcgatag cc                                              22

<210> SEQ ID NO 20
<211> LENGTH: 42
<212> TYPE: DNA
<213> ORGANISM: Artificial Sequence
<220> FEATURE:
<223> OTHER INFORMATION: primer

<400> SEQUENCE: 20
```

-continued

```
gaggatccat gaggagagag gggatcttga atggcatacg ac                    42
```

```
<210> SEQ ID NO 21
<211> LENGTH: 27
<212> TYPE: DNA
<213> ORGANISM: Artificial Sequence
<220> FEATURE:
<223> OTHER INFORMATION: primer

<400> SEQUENCE: 21
cgatcctgca ggacctcatc ggattgc                                     27

<210> SEQ ID NO 22
<211> LENGTH: 27
<212> TYPE: DNA
<213> ORGANISM: Artificial Sequence
<220> FEATURE:
<223> OTHER INFORMATION: primer

<400> SEQUENCE: 22
gtaggatccg cgcctaactt ctcaagc                                     27

<210> SEQ ID NO 23
<211> LENGTH: 25
<212> TYPE: DNA
<213> ORGANISM: Artificial Sequence
<220> FEATURE:
<223> OTHER INFORMATION: primer

<400> SEQUENCE: 23
atagaattca aaaggaaga gtatg                                        25

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
ctggggatcc aaaaacagga aggc                                        24

<210> SEQ ID NO 25
<211> LENGTH: 35
<212> TYPE: DNA
<213> ORGANISM: Artificial Sequence
<220> FEATURE:
<223> OTHER INFORMATION: primer

<400> SEQUENCE: 25
gagaaggtcg acgcagcatt tacttcaaag gcccc                            35

<210> SEQ ID NO 26
<211> LENGTH: 26
<212> TYPE: DNA
<213> ORGANISM: Artificial Sequence
<220> FEATURE:
<223> OTHER INFORMATION: primer

<400> SEQUENCE: 26
accgggtcga ccgtcgtttt acaacg                                      26

<210> SEQ ID NO 27
<211> LENGTH: 23
<212> TYPE: DNA
<213> ORGANISM: Artificial Sequence
```

-continued

```
<220> FEATURE:
<223> OTHER INFORMATION: primer

<400> SEQUENCE: 27
gggaattcat ggcctgcccg gtt                                        23

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
caaggatccc gaattaagga gtgg                                       24

<210> SEQ ID NO 29
<211> LENGTH: 27
<212> TYPE: DNA
<213> ORGANISM: Artificial Sequence
<220> FEATURE:
<223> OTHER INFORMATION: primer

<400> SEQUENCE: 29
ggtctgcagc tgcactaagc ggccgcc                                    27

<210> SEQ ID NO 30
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 30

Arg Arg Ile Leu Leu
1               5

<210> SEQ ID NO 31
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 31

Arg Arg Ser Phe Glu
1               5

<210> SEQ ID NO 32
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 32

Arg Arg Thr Leu Met
1               5

<210> SEQ ID NO 33
<211> LENGTH: 5
<212> TYPE: PRT
<213> ORGANISM: Artificial Sequence
<220> FEATURE:
```

```
<223> OTHER INFORMATION: predicted twin-arginine (RR-)signal peptides
      of B. subtilis

<400> SEQUENCE: 33

Arg Arg Ile Ile Ala
1               5

<210> SEQ ID NO 34
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 34

Arg Arg Leu Val Tyr
1               5

<210> SEQ ID NO 35
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 35

Arg Arg Arg Lys Leu
1               5

<210> SEQ ID NO 36
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 36

Arg Arg Lys Phe Ile
1               5

<210> SEQ ID NO 37
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 37

Arg Arg Gln Phe Leu
1               5

<210> SEQ ID NO 38
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 38

Arg Arg Leu Ile Ile
1               5
```

```
<210> SEQ ID NO 39
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 39

Arg Arg Asn Phe Lys
1               5

<210> SEQ ID NO 40
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 40

Arg Arg Lys Phe Ser
1               5

<210> SEQ ID NO 41
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 41

Arg Arg Ala Phe Leu
1               5

<210> SEQ ID NO 42
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 42

Arg Arg Met Lys Ile
1               5

<210> SEQ ID NO 43
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 43

Arg Arg Ser Cys Leu
1               5

<210> SEQ ID NO 44
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 44
```

```
Arg Arg Thr His Val
 1               5

<210> SEQ ID NO 45
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 45

Arg Arg Val Ala Ile
 1               5

<210> SEQ ID NO 46
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 46

Arg Arg Gln Phe Leu
 1               5

<210> SEQ ID NO 47
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 47

Arg Arg Phe Leu Leu
 1               5

<210> SEQ ID NO 48
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 48

Arg Arg Asn Thr Val
 1               5

<210> SEQ ID NO 49
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 49

Arg Arg Leu Leu Met
 1               5

<210> SEQ ID NO 50
<211> LENGTH: 5
<212> TYPE: PRT
<213> ORGANISM: Artificial Sequence
```

```
<220> FEATURE:
<223> OTHER INFORMATION: predicted twin-arginine (RR-)signal peptides
      of B. subtilis

<400> SEQUENCE: 50

Arg Arg Lys Ile Leu
1               5

<210> SEQ ID NO 51
<211> LENGTH: 5
<212> TYPE: PRT
<213> ORGANISM: Artificial Sequence
<220> FEATURE:
<223> OTHER INFORMATION: predicted twin-arginine (RR-)signal peptides
      of B. subtilis

<400> SEQUENCE: 51

Arg Arg Asp Ile Leu
1               5

<210> SEQ ID NO 52
<211> LENGTH: 42
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 52

Ser Pro Ala Gln Arg Arg Ile Leu Leu Tyr Ile Leu Ser Phe Ile Phe
1               5                   10                  15

Val Ile Gly Ala Val Val Tyr Phe Val Lys Ser Asp Tyr Leu Phe Thr
            20                  25                  30

Leu Ile Phe Ile Ala Ile Ala Ile Leu Phe
        35                  40

<210> SEQ ID NO 53
<211> LENGTH: 30
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 53

Met Val Ser Ile Arg Arg Ser Phe Glu Ala Tyr Val Asp Asp Met Asn
1               5                   10                  15

Ile Ile Thr Val Leu Ile Pro Ala Glu Gln Lys Glu Ile Met
            20                  25                  30

<210> SEQ ID NO 54
<211> LENGTH: 32
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 54

Met Ala Ala Tyr Ile Ile Arg Arg Thr Leu Met Ser Ile Pro Ile Leu
1               5                   10                  15

Leu Gly Ile Thr Ile Leu Ser Phe Val Ile Met Lys Ala Ala Pro Gly
            20                  25                  30

<210> SEQ ID NO 55
```

-continued

```
<211> LENGTH: 34
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 55

Met Lys Phe Val Lys Arg Arg Ile Ile Ala Leu Val Thr Ile Leu Met
1               5                   10                  15

Leu Ser Val Thr Ser Leu Phe Ala Leu Gln Pro Ser Ala Lys Ala Ala
            20                  25                  30

Glu His

<210> SEQ ID NO 56
<211> LENGTH: 32
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 56

Met Leu Lys Tyr Ile Gly Arg Arg Leu Val Tyr Met Ile Ile Thr Leu
1               5                   10                  15

Phe Val Ile Val Thr Val Thr Phe Phe Leu Met Gln Ala Ala Pro Gly
            20                  25                  30

<210> SEQ ID NO 57
<211> LENGTH: 42
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 57

Met Thr Ser Pro Thr Arg Arg Arg Thr Ala Lys Arg Arg Arg Arg Lys
1               5                   10                  15

Leu Asn Lys Arg Gly Lys Leu Leu Phe Gly Leu Leu Ala Val Met Val
            20                  25                  30

Cys Ile Thr Ile Trp Asn Ala Leu His Arg
        35                  40

<210> SEQ ID NO 58
<211> LENGTH: 54
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 58

Met Ala Tyr Asp Ser Arg Phe Asp Glu Trp Val Gln Lys Leu Lys Glu
1               5                   10                  15

Glu Ser Phe Gln Asn Asn Thr Phe Asp Arg Arg Lys Phe Ile Gln Gly
            20                  25                  30

Ala Gly Lys Ile Ala Gly Leu Ser Leu Gly Leu Thr Ile Ala Gln Ser
        35                  40                  45

Val Gly Ala Phe Glu Val
    50

<210> SEQ ID NO 59
```

```
<211> LENGTH: 36
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 59

Met Gly Gly Lys His Asp Ile Ser Arg Arg Gln Phe Leu Asn Tyr Thr
1               5                   10                  15

Leu Thr Gly Val Gly Gly Phe Met Ala Ala Ser Met Leu Met Pro Met
            20                  25                  30

Val Arg Phe Ala
        35

<210> SEQ ID NO 60
<211> LENGTH: 26
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 60

Met Leu Leu Lys Arg Arg Ile Gly Leu Leu Leu Ser Met Val Gly Val
1               5                   10                  15

Phe Met Leu Leu Ala Gly Cys Ser Ser Val
            20                  25

<210> SEQ ID NO 61
<211> LENGTH: 39
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 61

Met Lys Lys Thr Leu Thr Thr Ile Arg Arg Ser Ser Ile Ala Arg Arg
1               5                   10                  15

Leu Ile Ile Ser Phe Leu Leu Ile Leu Ile Val Pro Ile Thr Ala Leu
            20                  25                  30

Ser Val Ser Ala Tyr Gln Ser
        35

<210> SEQ ID NO 62
<211> LENGTH: 35
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 62

Met Lys Lys Arg Lys Arg Arg Asn Phe Lys Arg Phe Ile Ala Ala Phe
1               5                   10                  15

Leu Val Leu Ala Leu Met Ile Ser Leu Val Pro Ala Asp Val Leu Ala
            20                  25                  30

Lys Ser Thr
        35

<210> SEQ ID NO 63
<211> LENGTH: 33
<212> TYPE: PRT
```

<213> ORGANISM: Artificial Sequence
<220> FEATURE:
<223> OTHER INFORMATION: predicted twin-arginine signal peptides of B.
      subtilis

<400> SEQUENCE: 63

Lys Arg Arg Lys Phe Ser Ser Val Val Ala Ala Val Leu Ile Phe Ala
1               5                   10                  15

Leu Ile Phe Ser Leu Phe Ser Pro Gly Thr Lys Ala Ala Ala Ala Gly
            20                  25                  30

Ala

<210> SEQ ID NO 64
<211> LENGTH: 35
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 64

Met Glu Met Phe Asp Leu Glu Phe Met Arg Arg Ala Phe Leu Ala Gly
1               5                   10                  15

Gly Met Ile Ala Val Met Ala Pro Ile Leu Gly Val Tyr Leu Val Leu
            20                  25                  30

Arg Arg Gln
        35

<210> SEQ ID NO 65
<211> LENGTH: 26
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 65

Met Lys Lys Arg Arg Lys Ile Cys Tyr Cys Asn Thr Ala Leu Leu Leu
1               5                   10                  15

Met Ile Leu Leu Ala Gly Cys Thr Asp Ser
            20                  25

<210> SEQ ID NO 66
<211> LENGTH: 20
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 66

Met Arg Arg Ile Leu Ser Ile Leu Val Phe Ala Ile Met Leu Ala Gly
1               5                   10                  15

Cys Ser Ser Asn
            20

<210> SEQ ID NO 67
<211> LENGTH: 43
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 67

```
Met Ser Ala Gly Lys Ser Tyr Arg Lys Met Lys Gln Arg Met
1               5                   10                  15

Asn Met Lys Ile Ser Lys Tyr Ala Leu Gly Ile Leu Met Leu Ser Leu
                20                  25                  30

Val Phe Val Leu Ser Ala Cys Gly Asn Asn Asn
                35                  40
```

<210> SEQ ID NO 68
<211> LENGTH: 42
<212> TYPE: PRT
<213> ORGANISM: Artificial Sequence
<220> FEATURE:
<223> OTHER INFORMATION: predicted twin-arginine signal peptides of B. subtilis

<400> SEQUENCE: 68

```
Lys Lys Arg Val Ala Gly Trp Tyr Arg Arg Met Lys Ile Lys Asp Lys
1               5                   10                  15

Leu Phe Val Phe Leu Ser Leu Ile Met Ala Val Ser Phe Leu Phe Val
                20                  25                  30

Tyr Ser Gly Val Gln Tyr Ala Phe His Val
                35                  40
```

<210> SEQ ID NO 69
<211> LENGTH: 38
<212> TYPE: PRT
<213> ORGANISM: Artificial Sequence
<220> FEATURE:
<223> OTHER INFORMATION: predicted twin-arginine signal peptides of B. subtilis

<400> SEQUENCE: 69

```
Met Arg Arg Ser Cys Leu Met Ile Arg Arg Lys Arg Met Phe Thr
1               5                   10                  15

Ala Val Thr Leu Leu Val Leu Leu Val Met Gly Thr Ser Val Cys Pro
                20                  25                  30

Val Lys Ala Glu Gly Ala
        35
```

<210> SEQ ID NO 70
<211> LENGTH: 38
<212> TYPE: PRT
<213> ORGANISM: Artificial Sequence
<220> FEATURE:
<223> OTHER INFORMATION: predicted twin-arginine signal peptides of B. subtilis

<400> SEQUENCE: 70

```
Met Arg Ile Gln Lys Arg Arg Thr His Val Glu Asn Ile Leu Arg Ile
1               5                   10                  15

Leu Leu Pro Pro Ile Met Ile Leu Ser Leu Ile Leu Pro Thr Pro Pro
                20                  25                  30

Ile His Ala Glu Glu Ser
        35
```

<210> SEQ ID NO 71
<211> LENGTH: 32
<212> TYPE: PRT
<213> ORGANISM: Artificial Sequence
<220> FEATURE:
<223> OTHER INFORMATION: predicted twin-arginine signal peptides of B. subtilis

```
<400> SEQUENCE: 71

Met Leu Arg Asp Leu Gly Arg Arg Val Val Ala Ile Ala Ala Ile Leu
1               5                   10                  15

Ser Gly Ile Ile Leu Gly Gly Met Ser Ile Ser Leu Ala Asn Met Pro
            20                  25                  30

<210> SEQ ID NO 72
<211> LENGTH: 34
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 72

Met Lys Lys Met Ser Arg Arg Gln Phe Leu Lys Gly Met Phe Gly Ala
1               5                   10                  15

Leu Ala Ala Gly Ala Leu Thr Ala Gly Gly Tyr Gly Tyr Ala Arg
            20                  25                  30

Tyr Leu

<210> SEQ ID NO 73
<211> LENGTH: 28
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 73

Met Arg Arg Phe Leu Leu Asn Val Ile Leu Val Leu Ala Ile Val Leu
1               5                   10                  15

Phe Leu Arg Tyr Val His Tyr Ser Leu Glu Pro Glu
            20                  25

<210> SEQ ID NO 74
<211> LENGTH: 29
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 74

Met Phe Glu Ser Glu Ala Glu Leu Arg Arg Ile Arg Ile Ala Leu Val
1               5                   10                  15

Trp Ile Ala Val Phe Leu Leu Phe Gly Ala Cys Gly Asn
            20                  25

<210> SEQ ID NO 75
<211> LENGTH: 37
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 75

Met Gln Lys Tyr Arg Arg Arg Asn Thr Val Ala Phe Thr Val Leu Ala
1               5                   10                  15

Tyr Phe Thr Phe Phe Ala Gly Val Phe Leu Phe Ser Ile Gly Leu Tyr
            20                  25                  30

Asn Ala Asp Asn Leu
```

```
<210> SEQ ID NO 76
<211> LENGTH: 34
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 76

Met Met Leu Asn Met Ile Arg Arg Leu Leu Met Thr Cys Leu Phe Leu
1               5                   10                  15

Leu Ala Phe Gly Thr Thr Phe Leu Ser Val Ser Gly Ile Glu Ala Lys
            20                  25                  30

Asp Leu

<210> SEQ ID NO 77
<211> LENGTH: 44
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 77

Met Ala Glu Arg Val Arg Val Arg Val Arg Lys Lys Lys Ser Lys
1               5                   10                  15

Arg Arg Lys Ile Leu Lys Arg Ile Met Leu Leu Phe Ala Leu Ala Leu
            20                  25                  30

Leu Val Val Val Gly Leu Gly Gly Tyr Lys Leu Tyr
            35                  40

<210> SEQ ID NO 78
<211> LENGTH: 47
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 78

Met Ser Asp Glu Gln Lys Lys Pro Glu Gln Ile His Arg Arg Asp Ile
1               5                   10                  15

Leu Lys Trp Gly Ala Met Ala Gly Ala Ala Val Ala Ile Gly Ala Ser
            20                  25                  30

Gly Leu Gly Gly Leu Ala Pro Leu Val Gln Thr Ala Ala Lys Pro
            35                  40                  45

<210> SEQ ID NO 79
<211> LENGTH: 54
<212> TYPE: PRT
<213> ORGANISM: Bacillus subtilis

<400> SEQUENCE: 79

Met Ala Tyr Asp Ser Arg Phe Asp Glu Trp Val Gln Lys Leu Lys Glu
1               5                   10                  15

Glu Ser Phe Gln Asn Asn Arg Phe Asp Arg Arg Lys Phe Ile Gln Gly
            20                  25                  30

Ala Gly Lys Ile Ala Gly Leu Ser Leu Gly Leu Thr Ile Ala Gln Ser
            35                  40                  45

Val Gly Ala Phe Glu Val
```

50

<210> SEQ ID NO 80
<211> LENGTH: 65
<212> TYPE: PRT
<213> ORGANISM: Streptomyces coelicolor

<400> SEQUENCE: 80

Met Thr Pro Ala Asn His Gln Ala Pro Thr Ser Ala Pro Ser Pro Ala
1               5                   10                  15

Pro Ser Gln Ser Ser His Ala Pro Glu Leu Arg Ala Ala Ala Arg Ser
            20                  25                  30

Leu Gly Arg Arg Arg Phe Leu Thr Val Thr Gly Ala Ala Ala Ala Leu
        35                  40                  45

Ala Phe Ala Val Asn Leu Pro Ala Ala Gly Thr Ala Ser Ala Ala Glu
    50                  55                  60

Leu
65

<210> SEQ ID NO 81
<211> LENGTH: 60
<212> TYPE: PRT
<213> ORGANISM: Streptomyces coelicolor

<400> SEQUENCE: 81

Met Ala Pro Thr Gly Arg Pro Ser Ala Leu Ala Glu His Ala Phe Ser
1               5                   10                  15

Pro His Asp Ala Val Leu Gly Ala Ala Ala Arg His Leu Gly Arg Arg
            20                  25                  30

Arg Phe Leu Thr Val Thr Ala Ala Ala Ala Ala Leu Ala Phe Ser Thr
        35                  40                  45

Asn Leu Pro Ala Arg Gly Ala Val Ala Ala Pro Glu
    50                  55                  60

<210> SEQ ID NO 82
<211> LENGTH: 47
<212> TYPE: PRT
<213> ORGANISM: Streptomyces coelicolor

<400> SEQUENCE: 82

Met Thr Ser Arg His Arg Ala Ser Glu Asn Ser Arg Thr Pro Ser Arg
1               5                   10                  15

Arg Thr Val Val Lys Ala Ala Ala Ala Gly Ala Val Leu Ala Ala Pro
            20                  25                  30

Leu Ala Ala Ala Leu Pro Ala Gly Ala Ala Asp Ala Ala Pro Ala
        35                  40                  45

<210> SEQ ID NO 83
<211> LENGTH: 53
<212> TYPE: PRT
<213> ORGANISM: Streptomyces tendae

<400> SEQUENCE: 83

Met Thr Pro Ala Ala Arg Pro Ser Gln His Ala Pro Glu Leu Arg Ala
1               5                   10                  15

Ala Ala Arg His Leu Gly Arg Arg Arg Phe Leu Thr Val Thr Gly Ala
            20                  25                  30

Ala Ala Ala Leu Ala Phe Ala Val Asn Leu Pro Ala Ala Gly Thr Ala
        35                  40                  45

-continued

```
Ala Ala Ala Glu Leu
        50

<210> SEQ ID NO 84
<211> LENGTH: 43
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 84

Met Ser Pro Ala Gln Arg Arg Ile Leu Leu Tyr Ile Leu Ser Phe Ile
1               5                   10                  15

Phe Val Ile Gly Ala Val Val Tyr Phe Val Lys Ser Asp Tyr Leu Phe
            20                  25                  30

Thr Leu Ile Phe Ile Ala Ile Ala Ile Leu Phe
        35                  40

<210> SEQ ID NO 85
<211> LENGTH: 34
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 85

Met Lys Arg Arg Lys Phe Ser Ser Val Val Ala Ala Val Leu Ile Phe
1               5                   10                  15

Ala Leu Ile Phe Ser Leu Phe Ser Pro Gly Thr Lys Ala Ala Ala Ala
            20                  25                  30

Gly Ala

<210> SEQ ID NO 86
<211> LENGTH: 43
<212> TYPE: PRT
<213> ORGANISM: Artificial Sequence
<220> FEATURE:
<223> OTHER INFORMATION: predicted twin-arginine signal peptides of B.
      subtilis

<400> SEQUENCE: 86

Met Lys Lys Arg Val Ala Gly Trp Tyr Arg Arg Met Lys Ile Lys Asp
1               5                   10                  15

Lys Leu Phe Val Phe Leu Ser Leu Ile Met Ala Val Ser Phe Leu Phe
            20                  25                  30

Val Tyr Ser Gly Val Gln Tyr Ala Phe His Val
        35                  40
```